United States Patent [19]

Ito et al.

[11] Patent Number: 5,153,207
[45] Date of Patent: Oct. 6, 1992

[54] PIPERIDINE DERIVATIVE, METHOD FOR PREPARATION THEREOF, AND A PHARMACEUTICAL COMPOSITION COMPRISING THE SAME

[75] Inventors: Yasuo Ito, Katsuyama; Hideo Kato, Fukui; Eiichi Koshinaka, Katsuyama; Nobuo Ogawa, Katsuyama; Hiroyuki Nishino, Katsuyama; Jun Sakaguchi, Katsuyama, all of Japan

[73] Assignee: Hokuriku Pharmaceutical Co., Ltd., Katsuyama, Japan

[21] Appl. No.: 520,064

[22] Filed: May 3, 1990

[30] Foreign Application Priority Data

May 22, 1989 [JP] Japan .................................. 1-126596
Feb. 20, 1990 [JP] Japan .................................. 2-37397

[51] Int. Cl.$^5$ .................. A61K 31/445; C07D 211/06
[52] U.S. Cl. ...................................... 814/327; 546/221
[58] Field of Search .................. 546/221, 222; 514/327

[56] References Cited

U.S. PATENT DOCUMENTS 4,929,618 3/1990 Koda .................................. 546/221

FOREIGN PATENT DOCUMENTS

| 134124 | 3/1985 | European Pat. Off. . |
| 0134124 | 3/1985 | European Pat. Off. . |
| 226516 | 6/1987 | European Pat. Off. . |
| 0335586 | 10/1989 | European Pat. Off. . |
| 225465 | 1/1990 | Japan . |

OTHER PUBLICATIONS

Patent Abstracts of Japan vol. 11, No. 106 (C-414) (2553) Apr. 3, 1987, & JP-A-61 254559 (Terumo Corporation) Nov. 12, 1986, *the whole document*.

Primary Examiner—Alan L. Rotman
Assistant Examiner—Celia Chang
Attorney, Agent, or Firm—Oblon, Spivak, McClelland, Maier & Neustadt

[57] ABSTRACT

A piperidine derivative represented by the following general formula (I):

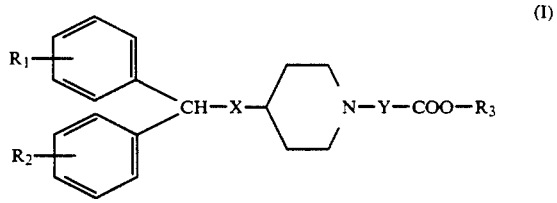

wherein $R_1$ and $R_2$ are the same or different and each independently represents a hydrogen atom, a halogen atom, a lower alkyl group, or a lower alkoxy group; $R_3$ represents a hydrogen atom or a lower alkyl group; X represents an oxygen atom or a sulfur atom; Y represents an alkylene group having 1 to 7 carbon atoms which may be optionally substituted with a lower alkyl group, or Y represents an —A—O—B— group wherein A and B are the same or different and each independently represents an alkylene group having 1 to 3 carbon atoms which may be optionally substituted with a lower alkyl group is disclosed. Also disclosed are a pharmacologically acceptable salt of a compound of formula (I), an antihistaminic and antiallergic agent comprising a compound of formula (I), a pharmaceutical composition comprising a compound of formula (I), and a method for the treatment of an allergic disease by administering a compound of formula (I).

5 Claims, No Drawings

PIPERIDINE DERIVATIVE, METHOD FOR PREPARATION THEREOF, AND A PHARMACEUTICAL COMPOSITION COMPRISING THE SAME

BACKGROUND OF THE INVENTION

1. Field of the Invention

The present invention relates to novel piperidine derivatives and pharmacologically acceptable salts thereof which have an antihistaminic and antiallergic activity and are useful for the treatment of, for example, bronchial asthma, allergic rhinitis, dermatosis, and urticaria, and to the method for preparation thereof.

The present invention also relates to a pharmaceutical composition comprising the effective amount of the same.

2. Description of the Prior Art

Among antihistaminic agents having diphenylmethoxypiperidine ring in their molecules, diphenylpyraline (The Merck Index, 11th edition, 3334) represented by the following formula:

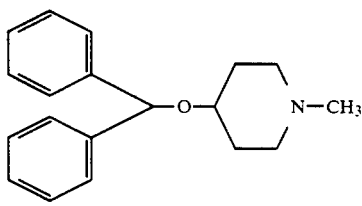

has been developed as a clinically available drug and is used for the treatment of such ailments as allergic rhinitis and dermatosis.

Japanese Unexamined Patent Publication No. 228059/1987 discloses TMK-688 (N-[2-[4-(diphenylmethoxy)piperidino]ethyl]-5-[4-(ethoxycarbonyloxy)-3-methoxyphenyl]-2,4-pentadienoylamide) represented by the following formula:

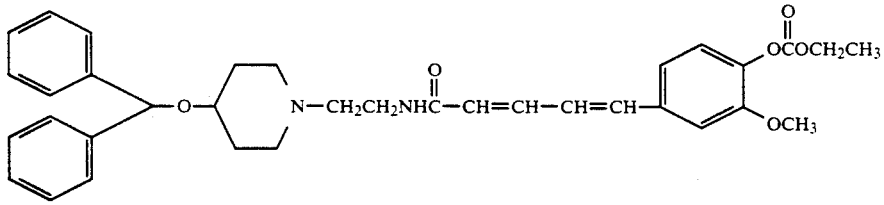

However, neither of the above discloses the compounds of the present invention.

A large number of antihistaminic agents have been developed so far and are used for the treatment of, for example, allergic dermatosis or rhinitis. However, adverse reactions of a central inhibitory action caused by the administration of the known antihistaminic agents such as sleepiness or sedation is found to be a great problem with these known agents. In addition, an anticholinergic action which is considered to be one of the possible reasons for hydrodipsia or mydriasis is another undesired adverse reaction of the antihistaminic agents. Various kinds of research have been conducted to solve the above problems, however, presently available antihistaminic agents are insufficient from a clinical point of view.

SUMMARY OF THE INVENTION

An object of the present invention is to provide novel compounds having an excellent antihistaminic activity as well as excellent antiallergic activity.

Another object of the present invention is to provide novel compounds which extensively eliminate undesired adverse reactions such as a central inhibitory action when administered for the treatment of such ailments as bronchial asthma, allergic rhinitis, dermatosis and urticaria.

A further object of the present invention is to provide a method for preparation of the above novel compounds. Yet another object is to provide a pharmaceutical composition comprising the novel compounds which is useful for the treatment of such ailments as bronchial asthma, allergic rhinitis, dermatosis and urticaria.

The inventors of the present invention have conducted various studies to achieve the foregoing objects and found that the objects can be effectively attained by providing novel piperidine derivatives of the present invention. These derivatives have potent antihistaminic and antiallergic activity and induce few adverse reactions such as central inhibition.

In accordance with the above objects, the present invention provides a piperidine derivative represented by the following general formula (I):

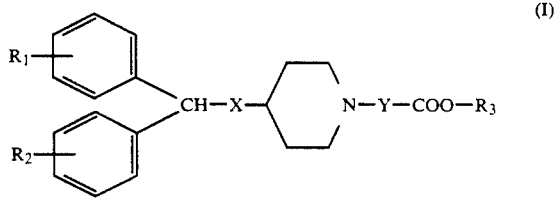

wherein $R_1$ and $R_2$ are the same or different and each independently represents a hydrogen atom, a halogen atom, a lower alkyl group, or a lower alkoxy group; $R_3$ represents a hydrogen atom or a lower alkyl group; X represents an oxygen atom or a sulfur atom; Y represents an alkylene group having 1 to 7 carbon atoms which may be optionally substituted with a lower alkyl group, or Y represents an —A—O—B— group wherein A and B are the same or different and each independently represents an alkylene group having 1 to 3 carbon atoms which may be optionally substituted with a lower alkyl group, and pharmacologically acceptable salts of the above compounds.

In accordance with another embodiment of the present invention, the present invention provides a process for preparing a piperidine derivative represented by the general formula (I). The process comprises the steps of reacting a piperidine derivative represented by the following general formula (II):

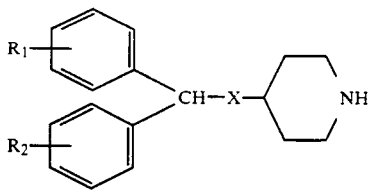

(II)

wherein $R_1$, $R_2$, and X are the same as those defined above, with a compound represented by Z—Y—COO—$R_3$ (IIIa) or $CH_2$=CHCOO—$R_3$ (IIIb) wherein $R_3$ and Y are the same as those defined above, and Z represents a halogen atom, in a solvent or without a solvent, and in the presence or absence of a base, followed by the step of hydrolysis in a solvent using an acid or a base, if necessary.

In accordance with yet another embodiment, the present invention provides an antihistaminic and antiallergic agent comprising an effective amount of a piperidine derivative represented by general formula (I).

In accordance with a further embodiment, the present invention provides a pharmaceutical composition for treatment of an allergic disease comprising an effective amount of a compound represented by general formula (I).

The invention also provides a method of treating an allergic disease comprising the step of administering to a mammal an effective amount of a piperidine derivative represented by general formula (I), a pharmacologically acceptable salt of the above compound, an antihistaminic and antiallergic agent comprising the same, or a pharmaceutical composition comprising the same.

Further objects, features and advantages of the present invention will become apparent from the Description of the Preferred Embodiments which follows, when read in light of the attached Examples.

DETAILED DESCRIPTION OF THE PREFERRED EMBODIMENTS

The present invention provides a piperidine derivative represented by the following general formula (I):

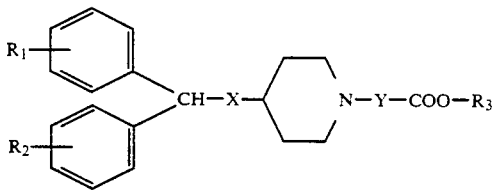

(I)

wherein $R_1$ and $R_2$ are the same or different and each independently represents a hydrogen atom, a halogen atom, a lower alkyl group, or a lower alkoxy group; $R_3$ represents a hydrogen atom or a lower alkyl group; X represents an oxygen atom or a sulfur atom; Y represents an alkylene group having 1 to 7 carbon atoms which may be optionally substituted with a lower alkyl group, or Y represents an —A—O—B— group wherein A and B are the same or different and each independently represents an alkylene group having 1 to 3 carbon atoms which may be optionally substituted with a lower alkyl group. The present invention also provides pharmacologically acceptable salts of the above compounds. In addition, the present invention provides a process for preparing the compounds of the general formula (I), and a pharmaceutical composition comprising an effective amount of the same together with a pharmaceutically acceptable carrier or coating.

In the above general formula (I), the halogen atom represented by $R_1$ and $R_2$ may be, for example, a fluorine atom, a chlorine atom, or bromine atom, the lower alkoxy group may be, for example, methoxy, ethoxy, n-propoxy, isopropoxy, n-butoxy, or isobutoxy group, the lower alkyl group represented by $R_1$, $R_2$, and $R_3$ or the lower alkyl group which may be a substituent of the alkylene group represented by Y, A, or B may be, for example, methyl, ethyl, n-propyl, isopropyl, n-butyl, isobutyl, or tert-butyl group. The alkylene group having 1 to 7 carbon atoms represented by Y which may be substituted with a lower alkyl group is preferably an alkylene group having 4 to 7 carbon atoms.

Preferred examples of the present invention include:
(±)-4-[(4-methylphenyl)phenylmethoxy]-1-piperidinecaproic acid;
4-(diphenylmethoxy)-1-piperidinepropionic acid;
(±)-4-[(4-methylphenyl)phenylmethoxy]-1-piperidinepropionic acid;
(±)-4-[(4-methylphenyl)phenylmethoxy]-1-piperidinebutyric acid;
(±)-4-[(4-methylphenyl)phenylmethoxy]-1-piperidinevaleric acid;
(±)-4-[(4-methylphenyl)phenylmethoxy]-1-piperidineheptanoic acid;
(±)-4-[(4-methylphenyl)phenylmethoxy]-1-piperidineoctanoic acid;
(±)-4-[(4-ethylphenyl)phenylmethoxy]-1-piperidinecaproic acid;
(±)-4-[(4-methoxyphenyl)phenylmethoxy]-1-piperidinepropionic acid;
(±)-4-[(4-methoxyphenyl)phenylmethoxy]-1-piperidinebutyric acid;
(±)-4-[(4-methoxyphenyl)phenylmethoxy]-1-piperidinecaproic acid;
(±)-4-[(2-chlorophenyl)phenylmethoxy]-1-piperidinebutyric acid;
(±)-4-[(4-fluorophenyl)phenylmethoxy]-1-piperidinebutyric acid;
(±)-4-[(4-fluorophenyl)phenylmethoxy]-1piperidinevaleric acid;
4-[bis(4-fluorophenyl)methoxy]-1-piperidinevaleric acid;
(+)-4-[(4-methylphenyl)phenylmethoxy]-1-piperidinecaproic acid;
(−)-4-[(4-methylphenyl)phenylmethoxy]-1-piperidinecaproic acid;
(+)-4-[(4-ethylphenyl)phenylmethoxy]-1-piperidinecaproic acid;
(−)-4-[(4-ethylphenyl)phenylmethoxy]-1-piperidinecaproic acid;
(+)-4-[(4-methoxyphenyl)phenylmethoxy]-1-piperidinecaproic acid;
(−)-4-[(4-methoxyphenyl)phenylmethoxy]-1-piperidinecaproic acid;
(±)-methyl 4-[(4-methylphenyl)phenylmethoxy]-1-piperidinecaproate;
(±)-ethyl 4-[(4-methylphenyl)phenylmethoxy]-1-piperidinecaproate;
ethyl 4-(diphenylmethoxy)-1-piperidinepropionate;
(±)-ethyl 4-[(4-methylphenyl)phenylmethoxy]-1-piperidinepropionate;
(±)-ethyl 4-[(4-methylphenyl)phenylmethoxy]-1-piperidinebutyrate;

(±)-ethyl 4-[(4-methylphenyl)phenylmethoxy]-1-piperidinevalerate;
(±)-methyl 4-[(4-methylphenyl)phenylmethoxy]-1-piperidineheptanoate;
(±)-methyl 4-[(4-methylphenyl)phenylmethoxy]-1-piperidineoctanoate;
(±)-methyl 4-[(4-ethylphenyl)phenylmethoxy]-1-piperidinecaproate;
(±)-ethyl 4-[(4-methoxyphenyl)phenylmethoxy]-1-piperidinepropionate;
(±)-ethyl 4-[(4-methoxyphenyl)phenylmethoxy]-1-piperidinebutyrate;
(±)-methyl 4-[(4-methoxyphenyl)phenylmethoxy]-1-piperidinecaproate;
(±)-ethyl 4-[(2-chlorophenyl)phenylmethoxy]-1-piperidinebutyrate;
(±)-ethyl 4-[(4-fluorophenyl)phenylmethoxy]-1-piperidinebutyrate;
(±)-ethyl 4-[(4-fluorophenyl)phenylmethoxy]-1-piperidinevalerate; 4-[bis(4-fluorophenyl) methoxy]-1-piperidinevaleric acid;
(±)-methyl 4-[(4-methylphenyl)phenylmethoxy]-1-piperidinecaproate;
(±)-ethyl 4-[(4-methylphenyl)phenylmethoxy]-1-piperidinecaproate;
(−)-methyl 4-[(4-methylphenyl)phenylmethoxy]-1-piperidinecaproate;
(−)-ethyl 4-[(4-methylphenyl)phenylmethoxy]-1-piperidinecaproate;
(+)-methyl 4-[(4-ethylphenyl)phenylmethoxy]-1-piperidinecaproate;
(−)-methyl 4-[(4-ethylphenyl)phenylmethoxy]-1-piperidinecaproate;
(+)-methyl 4-[(4-methoxyphenyl)phenylmethoxy]-1-piperidinecaproate;
(−)-methyl 4-[(4-methoxyphenyl)phenylmethoxy]-1-piperidinecaproate;
(+)-ethyl 4-[(4-ethylphenyl)phenylmethoxy]-1-piperidinecaproate;
(−)-ethyl 4-[(4-ethylphenyl)phenylmethoxy]-1-piperidinecaproate;
(+)-ethyl 4-[(4-methoxyphenyl)phenylmethoxy]-1-piperidinecaproate; and
(−)-ethyl 4-[(4-methoxyphenyl)phenylmethoxy]-1-piperidinecaproate.

The compounds of the present invention represented by the above general formula (I) may be converted to pharmacologically acceptable salts, if desired, and may then be reconverted to produce the free compound from the obtained salts.

The pharmacologically acceptable salts of the compounds of the present invention represented by the general formula (I) may be acid addition salts or alkali addition salts. Examples of the acid addition salts include mineral acids such as for example hydrochloride, hydrobromide, sulfate, nitrate, and phosphate, and organic acid salt such as for example acetate, maleate, fumarate, malate, citrate, oxalate, lactate, and tartarate. Examples of the alkali addition salts include metal salts such as for example sodium, potassium, and calcium salt, and organic alkali salts such as for example ammonium salts, methylamine, ethylamine, dimethylamine, triethylamine, ethanolamine, piperidine, and piperazine salts.

The compound of the present invention represented by the above general formula (I) may have one or more asymmetric carbon atoms in the molecule, and consequently, optically active compounds and diastereoisomers may exist, which are incorporated within the scope of the present invention.

The novel piperidine derivatives of the present invention represented by the above general formula (I) can be prepared by reacting a piperidine derivative represented by the following general formula (II):

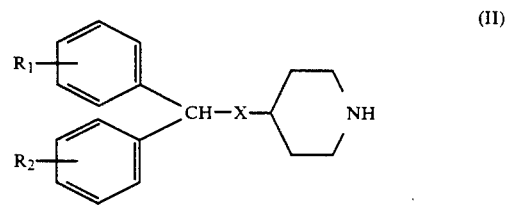

wherein $R_1$, $R_2$, and X are the same as those defined above, with a compound represented by Z—Y—COO—$R_3$ (IIIa) or $CH_2$=CHCOO—$R_3$ (IIIb) wherein $R_3$ and Y are the same as those defined above, and Z represents a halogen atom, in a solvent or without a solvent in the presence or absence of a base, and followed by hydrolysis in a solvent by using an acid or a base, if necessary.

Any inert solvent may be used in the condensation process of the present invention. Examples of the inert solvent include benzene, toluene, tetrahydrofuran, dioxane, acetone, acetonitrile, methanol, ethanol, isopropanol, n-butanol, dimethyl sulfoxide, and N,N-dimethylformamide.

Examples of the base used in the process of the present invention include potassium carbonate, sodium carbonate, pyridine, and triethylamine. The reaction may be carried out at from 0° to 200° C.

For the hydrolysis process, an acid such as for example hydrochloric acid or sulfuric acid, or a base such as for example sodium hydroxide, potassium hydroxide, potassium carbonate, sodium carbonate, or sodium bicarbonate may be used. A solvent used in the hydrolysis may be, for example, water, methanol, ethanol, acetone, or tetrahydrofuran, and the hydrolysis may be carried our at from 0° to 100° C.

In addition, the compounds represented by the above general formula (II), used as starting materials for the above process, are, with few exceptions, novel compounds which may be prepared according to the following process:

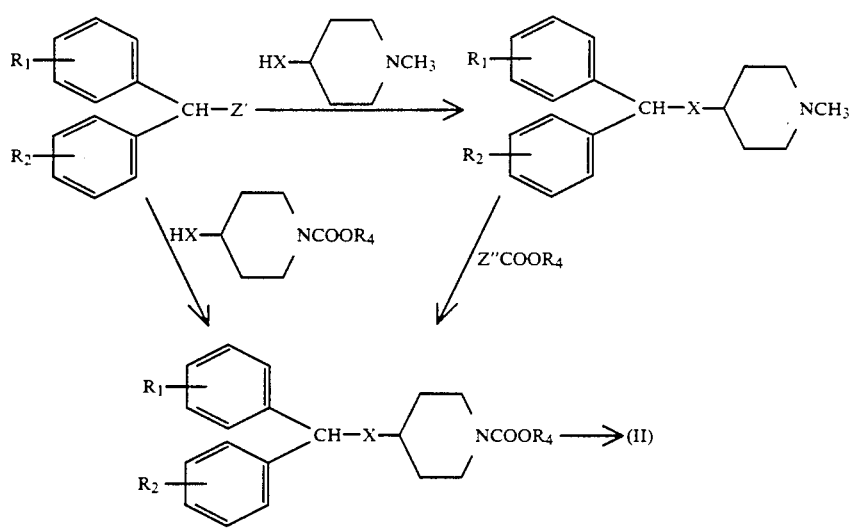

wherein, $R_1$, $R_2$, and X are the same as those defined above, Z' and Z" are the same or different and each represents a halogen atom, and $R_4$ represents a lower alkyl group.

The novel piperidine compound of the present invention represented by the above general formula (I) and the pharmacologically acceptable salt thereof has an excellent antihistaminic and antiallergic activity, and thus is quite useful for the treatment of an allergic disease, such as, for example, bronchial asthma, allergic rhinitis, dermatosis, and urticaria.

The piperidine compounds of the present invention and their pharmacologically acceptable salts may be administered orally or parenterally to a patient as a pharmaceutical composition which comprises an effective amount of said compound or said salt together with a pharmaceutically acceptable carrier or coating.

The pharmaceutical composition suitable for oral administration may be, for example, tablet, capsule, powder, subtilized granule, granule, solution, or syrup. The pharmaceutical composition suitable for parenteral administration may be injection, suppository, inhalant, eye drop, nasal drop, ointment, or cataplasm. The pharmaceutically acceptable carrier or coating used for the preparation of the pharmaceutical composition may be excipient, disintegrant or agent for accelerating disintegration, binder, lubricant, coating agent, pigment, diluent, base, solubilizing agent, solubilizer, isotonicity, pH adjusting agent, stabilizer, propellant, and adhesive.

For the preparation of the pharmaceutical composition suitable for oral administration, dermal administration, or mucosal application, the coating or carrier may comprise the following: an excipient such as for example glucose, lactose, D-mannitol, starch, or crystalline cellulose; a disintegrant or an agent for accelerating disintegration such as for example carboxymethylcellulose, starch, or calcium carboxymethylcellulose; a binder such as for example hydroxypropylcellulose, hydroxypropylmethylcellulose, polyvinylpyrrolidone, or gelatin; a lubricant such as for example magnesium stearate or talc; a coating agent such as for example hydroxypropylmethylcellulose, sucrose, or titanium oxide; a base such as for example petrolatum, liquid paraffin, polyethyleneglycol, or hard fat; a propellant such as for example from, diethylether, or compressed gas; and adhesive such as for example sodium polyacrylate, polyvinylalcohol, methylcellulose, polyisobutylene, or polybutene; or a base sheet such as for example cloth or plastic sheet. The pharmaceutical composition suitable for injection may comprise the following: a solubilizing agent or a solubilizer, e.g., distilled water for injection, saline, or propylene glycol which is useful for an aqueous composition or a composition for preparing aqueous solution before use; an isotonicity agent such as for example glucose, sodium chloride, D-mannitol, or glycerin; and a pH adjusting agent such as for example an inorganic or organic acid or an inorganic or organic base.

The dose of the pharmaceutical composition of the present invention for an adult patient may generally be from about 1 to 300 mg per day for oral administration, which may be increased or decreased depending on the conditions of the patient to be treated.

The present invention will be further illustrated by the following Examples and Reference Examples. The Examples are given by way of illustration only and are not to be construed as limiting.

Examples and Reference Examples

The following example shows the excellent effectiveness of the present compounds. The results of 48 hr homologous passive cutaneous anaphylaxis (PCA) in rats with the monitoring of antiallergic activity and potentiation of hexobarbital-induced anesthesia in mice with the monitoring of central nervous depressive activity are summarized in Table 1. The following compounds were used as the reference compounds.

Reference compound A: diphenylpyraline hydrochloride
Reference compound B: TMK-688
1.48 hr homologous passive cutaneous anaphylaxis (PCA) in rats
  a) Preparation of DNP-As and rat anti-DNP-As serum Ascaris extract coupled with 2,4-dinitrophenyl group (DNP-As) was prepared by the method of Koda et al. (Folia pharmacol. japon., 78, 319–334, 1981) and anti-DNP-As containing IgE antibody serum was prepared by the method of Tada and Okumura (J. Immunol., 106, 1019-1025, 1971). The PCA titer of the antiserum was estimated as 1:128 by 48 hr PCA in rats.

b) 48 hr homologous passive cutaneous anaphylaxis (PCA) in rats

Male Wistar rats weighing 160 to 220 g were sensitized passively by intradermal injection in the back, of 0.05 ml of anti-DNP-As serum, diluted 21-fold with saline. After 48 hr, the animals (18-20 hr fasted) were given i.v. 0.5 ml of 1% Evans blue solution containing 1 mg of DNP-As. After additional thirty minutes, the animals were killed by stunning and the skins were removed. The intensity of the response was evaluated by assaying the amount of dye leaked according to the method of Katayama et al. (Microbiol. Immunol., 22, 89-101, 1978). The percent inhibition of PCA was calculated using the following formula:

$$\text{Percent inhibition} = \frac{\text{Amount of dye leaked of control} - \text{Amount of dye leaked of test compound}}{\text{Amount of dye leaked of control}} \times 100$$

Test compounds were given orally in a dose 1.0 mg/kg 1 hr prior to challenge with antigen. As a control, 5 ml/kg of vehicle (0.5% CMC) alone were given in a similar manner.

The results are shown in Table 1.

2. Potentiation of hexobarbital-induced anesthesia in mice

The loss of righting reflex induced by hexobarbital was used as an index of anesthesia. Groups of eight male ddY mice (20-24 hr fasted) weighing 19 to 27 g were treated orally with the test compounds (30 mg/kg) or vehicle. Thirty minutes later, 80 mg/kg of hexobarbital sodium were injected i.p. to the animals and the duration of loss of righting reflex was observed. The percent increase of sleeping time was calculated using the following formula:

$$\text{Percent increase} = \frac{\text{Sleeping time of test compound} - \text{Sleeping time of control}}{\text{Sleeping time of control}} \times 100$$

The results are listed in Table 1.

TABLE 1

| Test compound | the percent inhibition of PCA in rats (%, 1 mg/kg, p.o.) | the percent increase of hexobarbital-induced anesthesia in mice (%, 30 mg/kg, p.o.) |
|---|---|---|
| Example 1 | 77 | 16 |
| Example 62 | 56 | 29 |
| Example 64 | 68 | −8 |
| Example 65 | 62 | 29 |
| Example 70 | 51 | −2 |
| Example 71 | 65 | 3 |
| Example 72 | 63 | 12 |
| Example 73 | 67 | 2 |
| Example 74 | 59 | 21 |
| Example 77 | 68 | 24 |
| Example 86 | 60 | 4 |
| Example 87 | 54 | 18 |
| Example 89 | 71 | 20 |
| Example 112 | 53 | 29 |
| Example 115 | 73 | 21 |
| Example 116 | 83 | 31 |
| Example 120 | 64 | −12 |
| Example 125 | 55 | 29 |
| Example 126 | 36 | −1 |
| Reference compound A | −1 | 75 |
| Reference compound B | 8 | 35 |

The present compounds exhibited a more potent antiallergic activity and less potent central nervous depressive activity than the reference compounds.

Reference 1

(±)-4-[(4-Fluorophenyl)phenylmethoxy]-1-methyl-piperidine hydrochloride

A mixture of 48.6 g of 4-fluorobenzhydryl chloride, 25.3 g of 4-hydroxy-1-methylpiperidine and 18.3 g of potassium carbonate was heated with stirring at 140° C. for 5.5 hours. After cooling, water was added to the reaction mixture and extracted with ethyl acetate. The extract was washed with water, dried and concentrated. The residue was taken up in ether and the organic layer was extracted with hydrochloric acid. The aqueous layer was made alkaline with potassium carbonate and extracted with ether. The extract was washed with water, dried and concentrated to give 53.3 g of reddish brown liquid, which was converted to the hydrochloride in the usual manner and then recrystallized from a mixture of ethanol and ether to give colorless needles, mp 192°-193° C.

Analysis for $C_{19}H_{22}FNO\cdot HCl\cdot 1/4H_2O$: Calculated C, 67.05; H, 6.96; N, 4.12 Found C, 67.13; H, 6.89; N, 4.08

Reference 2

4-(Diphenylmethylthio)-1-methylpiperidine hydrochloride

A mixture of 12.7 g of benzhydryl chloride, 8.20 g of 4-mercapto-1-methylpiperidine and 8.64 g of potassium carbonate was heated with stirring at 150° C. for 3.5 hours. After cooling, water was added to the reaction mixture and extracted with benzene. The benzene layer was extracted with hydrochloric acid. The aqueous layer was made alkaline with potassium carbonate and extracted with ether. The extract was washed with water, dried and concentrated to give 10.3 g of brown liquid, which was purified by column chromatography on silica gel [eluent: chloroform-methanol (50:1)] to give an oily residue. The residue was solidified with n-hexane to give 6.41 g of pale brown crystals, m.p. 72°~74° C., which were converted to the hydrochloride in the usual manner and then recrystallized from a mixture of acetone and ether to give pale yellow needles, mp 182°~183° C.

Analysis for $C_{19}H_{23}NS\cdot HCl$: Calculated C, 68.34; H, 7.24; N, 4.19 Found C, 68.21; H, 7.05; N, 4.18

The compounds of References 3 to 12 were prepared in the same manner as described in References 1 and 2.

Reference 3

(±)-4-[(2-chlorophenyl)phenylmethoxy]-1-methyl-piperidine fumarate

Colorless crystals, mp 156°~157° C. (EtOH-Et$_2$O).

Analysis for $C_{19}H_{22}ClNO\cdot C_4H_4O_4$: Calculated C, 63.96; H, 6.07; N, 3.24 Found C, 63.97; H, 6.04; N, 3.27

Reference 4

(±)-4-[(3-Chlorophenyl)phenylmethoxy]-1-methylpiperidine fumarate

Colorless prisms, mp 148°~150° C. (EtOH-Et$_2$O).

Analysis for C$_{19}$H$_{22}$ClNO.C$_4$H$_4$O$_4$: Calculated C, 63.96; H, 6.07; N, 3.24 Found C, 63.90; H, 6.17; N, 3.20

Reference 5

(±)-1-Methyl-4-[(4-methylphenyl)phenylmethoxy]-piperidine maleate

Colorless needles, mp 132°~133° C. (EtOH-Et$_2$O).

Analysis for C$_{20}$H$_{25}$NO.C$_4$H$_4$O$_4$: Calculated C, 70.05; H, 7.10; N, 3.40 Found C, 69.85; H, 7.06; N, 3.48

Reference 6

4-[Bis(4-fluorophenyl)methoxy]-1-methylpiperidine fumarate

Colorless needles, mp 147°~148° C. (EtOH-Et$_2$O).

Analysis for C$_{19}$H$_{21}$F$_2$NO.C$_4$H$_4$O$_4$: Calculated C, 63.73; H, 5.81; N, 3.23 Found C, 63.77; H, 5.83; N, 3.22

Reference 7

(±)-4-[(4-Ethylphenyl)phenylmethoxy]-1-methylpiperidine fumarate

Colorless crystals, mp 171°~174° C. (EtOH-Et$_2$O).

Analysis for C$_{21}$H$_{27}$NO.C$_4$H$_4$O$_4$: Calculated C, 70.57; H, 7.34; N, 3.29 Found C, 70.48; H, 7.22; N, 3.23

Reference 8

(±)-1-Methyl-4-[(4-n-propylphenyl)phenylmethoxy]-piperidine hydrochloride

Colorless crystals, mp 166°~169° C. (EtOH-Et$_2$O).

Analysis for C$_{22}$H$_{29}$NO.HCl.H$_2$O: Calculated C, 69.91; H, 8.53; N, 3.71 Found C, 70.12; H, 8.33; N, 3.66

Reference 9

(±)-4-[(4-n-Butylphenyl)phenylmethoxy]-1-methylpiperidine fumarate

Colorless crystals, mp 96°~98° C. (AcOEt).

Analysis for C$_{23}$H$_{31}$NO.C$_4$H$_4$O$_4$: Calculated C, 71.50; H, 7.78; N, 3.09 Found C, 71.20; H, 7.98; N, 3.18

Reference 10

(±)-4-[(4-tert-Butylphenyl)phenylmethoxy]-1-methylpiperidine hydrochloride

Colorless crystals, mp 212°~215° C. (EtOH-AcOEt).

Analysis for C$_{23}$H$_{31}$NO.HCl: Calculated C, 73.87; H, 8.62; N, 3.75 Found C, 73.76; H, 8.65; N, 3.73

Reference 11

4-[Bis(4-methylphenyl)methoxy]-1-methylpiperidine fumarate

Colorless crystals, mp 135°~137° C. (Me$_2$CO).

Analysis for C$_{21}$H$_{27}$NO.C$_4$H$_4$O$_4$: Calculated C, 70.57; H, 7.34; N, 3.29 Found C, 70.39; H, 7.35; N, 3.38

Reference 12

(±)-4-[4-Ethoxyphenyl)phenylmethoxy]-1-methylpiperidine fumarate

Colorless needles, mp 164°~165.5° C. (EtOH).

Analysis for C$_{21}$H$_{27}$NO$_2$.C$_4$H$_4$O$_4$: Calculated C, 68.01; H, 7.08; N, 3.17 Found C, 67.83; H, 7.28; N, 3.08

Reference 13

(±)-Ethyl 4-[(4-fluorophenyl)phenylmethoxy]-1-piperidinecarboxylate

A quantity of 92.9 g of ethyl chlorocarbonate was added dropwise to a solution of 50.2 g of (±)-4-[(4-fluorophenyl)phenylmethoxy]-1-methylpiperidine in 200 ml of toluene, and the resulting solution was refluxed for 8 hours. After cooling, the reaction solution was washed with hydrochloric acid and water, dried and concentrated to give 51.9 g of yellowish brown liquid.

Mass spectrum m/z: 357 (M+).

IR spectrum $\nu$(liq) cm$^{-1}$: 1698 (COO—).

NMR spectrum $\delta$(CDCl$_3$) ppm: 1.24 (3H, t, J=7 Hz), 1.54–1.96 (4H, m), 3.00–3.36 (2H, m), 3.40–3.94 (3H, m), 4.11 (2H, q, J=7 Hz), 5.50 (1H, s), 6.97 (2H, t, J=9 Hz), 7.15–7.50 (7H, m).

Reference 14

Ethyl 4-(diphenylmethylthio)-1-piperidinecarboxylate

A quantity of 11.6 g of ethyl chlorocarbonate was added dropwise to a solution of 6.40 g of 4-(diphenylmethylthio)-1-methylpiperidine in 30 ml of toluene, and then the resulting mixture was refluxed for 2.5 hours. After cooling, the reaction mixture was washed with hydrochloric acid and water, dried and concentrated to give 7.73 g of pale yellowish brown solid, which were recrystallized from n-hexane to give colorless needles, mp 70°~71° C.

Analysis for C$_{21}$H$_{25}$NO$_2$S: Calculated C, 70.95; H, 7.09; N, 3.94 Found C, 71.09; H, 6.89; N, 3.92

The compounds of References 15 to 25 were prepared in the same manner as described in References 13 and 14.

Reference 15

(±)-Ethyl 4-[(2-chlorophenyl)phenylmethoxy]-1-piperidinecarboxylate

Pale brown liquid.

Mass spectrum m/z: 373, 375 (3:1, M+).

IR spectrum $\nu$(liq) cm$^{-1}$: 1700 (COO—).

NMR spectrum $\delta$(CDCl$_3$) ppm: 1.24 (3H, t, J=7 Hz), 1.40–2.10 (4H, m), 3.00–4.00 (5H, m), 4.11 (2H, q, J=7 Hz), 5.99 (1H, s), 7.00–7.70 (9H, m).

Reference 16

(±)-Ethyl 4-[(3-chlorophenyl)phenylmethoxy]-1-piperidinecarboxylate

Pale brown liquid.

Mass spectrum m/z: 373, 375 (3:1, M+).

IR spectrum $\nu$(liq) cm$^{-1}$: 1698 (COO—).

NMR spectrum $\delta$(CDCl$_3$) ppm: 1.25 (3H, t, J=7 Hz), 1.50–2.05 (4H, m), 3.00–4.00 (5H, m), 4.12 (2H, q, J=7 Hz), 5.47 (1H, s), 7.00–7.55 (9H, m).

Reference 17

(±)-Ethyl 4-[(4-chlorophenyl)phenylmethoxy]-1-piperidinecarboxylate

Pale yellow liquid.

Mass spectrum m/z: 373, 375 (3:1, M+).

IR spectrum $\nu$(liq) cm$^{-1}$: 1698 (COO—).

NMR spectrum δ(CDCl₃) ppm: 1.24 (3H, t, J=7 Hz), 1.45-2.00 (4H, m), 3.00-3.95 (5H, m), 4.11 (2H, q, J=7 Hz), 5.48 (1H, s), 7.10-7.50 (9H, m).

Reference 18

(±)-Ethyl 4-[(4-methylphenyl)phenylmethoxy]-1-piperidinecarboxylate

Pale yellowish brown liquid.
Mass spectrum m/z: 353(M+).
IR spectrum ν(liq) cm⁻¹: 1700 (COO—).
NMR spectrum δ(CDCl₃) ppm: 1.24 (3H, t, J=7 Hz), 1.40-2.00 (4H, m), 2.31 (3H, s), 3.00-3.96 (5H, m), 4.11 (2H, q, J=7 Hz), 5.49 (1H, s), 7.00-7.50 (9H, m).

Reference 19

(±)-Ethyl 4-[(4-methoxyphenyl)phenylmethoxy]-1-piperidinecarboxylate

Pale brown liquid.
Mass spectrum m/z: 369(M+).
IR spectrum ν(liq) cm⁻¹: 1696 (COO—).
NMR spectrum δ(CDCl₃) ppm: 1.24 (3H, t, J=7 Hz), 1.50-2.00 (4H, m), 3.00-3.95 (5H, m), 3.77 (3H, s), 4.11 (2H, q, J=7 Hz), 5.48 (1H, s), 6.84 (2H, d, J=9 Hz), 7.10-7.50 (5H, m), 7.24 (2H, d, J=9 Hz).

Reference 20

(±)-Ethyl 4-[(4-ethylphenyl)phenylmethoxy]-1-piperidinecarboxylate

Pale brown liquid.
Mass spectrum m/z: 367(M+).
IR spectrum ν(liq) cm⁻¹: 1700 (COO—).
NMR spectrum δ(CDCl₃) ppm: 1.21 (3H, t, J=7 Hz), 1.24 (3H, t, J=7 Hz), 1.55-2.04 (4H, m), 2.62 (2H, q, J=7 Hz), 3.00-3.97 (5H, m), 4.11 (2H, q, J=7 Hz), 5.50 (1H, s), 7.00-7.50 (9H, m).

Reference 21

(±)-Ethyl 4-[(4-n-propylphenyl)phenylmethoxy]-1-piperidinecarboxylate

Yellow liquid.
Mass spectrum m/z: 381(M+).
IR spectrum ν(liq) cm⁻¹: 1702 (COO—).
NMR spectrum δ(CDCl₃) ppm: 0.92 (3H, t, J=7 Hz), 1.24 (3H, t, J=7 Hz), 1.36-2.04 (6H, m), 2.55 (2H, t, J=7 Hz), 3.00-3.96 (5H, m), 4.11 (2H, q, J=7 Hz), 5.49 (1H, s), 7.00-7.46 (9H, m).

Reference 22

(±)-Ethyl 4-[(4-n-butylphenyl)phenylmethoxy]-1-piperidinecarboxylate

Yellow liquid.
Mass spectrum m/z: 395(M+).
IR spectrum ν(liq) cm⁻¹: 1702 (COO—).
NMR spectrum δ(CDCl₃) ppm: 0.91 (3H, t, J=7 Hz), 1.24 (3H, t, J=7 Hz), 1.09-2.02 (8H, m), 2.57 (2H, t, J=7 Hz), 3.04-3.96 (5H, m), 4.11 (2H, q, J=7 Hz), 5.49 (1H, s), 7.04-7.46 (9H, m).

Reference 23

(±)-Ethyl 4-[(4-tert-butylphenyl)phenylmethoxy]-1-piperidinecarboxylate

Yellow liquid.
Mass spectrum m/z: 395(M+).
IR spectrum ν(liq) cm⁻¹: 1702 (COO—).
NMR spectrum δ(CDCl₃) ppm: 1.24 (3H, t, J=7 Hz), 1.29 (9H, s), 1.50-1.90 (4H, m), 3.00-3.96 (5H, m), 4.11 (2H, q, J=7 Hz), 5.50 (1H, s), 7.10-7.46 (9H, m).

Reference 24

Ethyl 4-[bis(4-methylphenyl)methoxy]-1-piperidinecarboxylate

Orange liquid.
Mass spectrum m/z: 367(M+).
IR spectrum ν(liq) cm⁻¹: 1700 (COO—).
NMR spectrum δ(CDCl₃) ppm: 1.24 (3H, t, J=7 Hz), 1.39-2.00 (4H, m), 2.31 (6H, s), 2.98-3.95 (5H, m), 4.11 (2H, q, J=7 Hz), 5.46 (1H, s), 7.00-7.37 (8H, m).

Reference 25

(±)-Ethyl 4-[(4-ethoxyphenyl)phenylmethoxy]-1-piperidinecarboxylate

Pale brown liquid.
Mass spectrum m/z: 383(M+).
IR spectrum ν(liq) cm⁻¹: 1700 (COO—).
NMR spectrum δ(CDCl₃) ppm: 1.24 (3H, t, J=7 Hz), 1.39 (3H, t, J=7 Hz), 1.54-2.00 (4H, m), 3.01-3.88 (5H, m), 4.01 (2H, q, J=7 Hz), 4.12 (2H, q, J=7 Hz), 5.47 (1H, s), 6.83 (2H, d, J=9 Hz), 7.08-7.47 (5H, m), 7.22 (2H, d, J=9 Hz).

Reference 26

(±)-4-[(4-Fluorophenyl)phenylmethoxy]piperidine hydrochloride

A mixture of 51.4 g of (±)-ethyl 4-[(4-fluorophenyl)phenylmethoxy]-1-piperidinecarboxylate, 50.0 g of sodium hydroxide, 52.5 ml of water and 300 ml of ethanol was refluxed for 22 hours and concentrated. Water was added to the residue and extracted with ether. The ether layer was washed with water and extracted with hydrochloric acid. The aqueous layer was made alkaline with potassium carbonate and extracted with ether. The extract was washed with water, dried and concentrated to give 38.3 g of pale yellowish brown liquid, which was converted to the hydrochloride in the usual manner and then recrystallized from a mixture of ethanol and ether to give colorless needles, mp 173°~174° C.

Analysis for $C_{18}H_{20}FNO \cdot HCl$: Calculated C, 67.18; H, 6.58; N, 4.35 Found C, 67.19; H, 6.53; N, 4.32

Reference 27

4-(Diphenylmethylthio)piperidine hydrochloride

A mixture of 7.60 g of ethyl 4-(diphenylmethylthio)-1-piperidinecarboxylate, 5.12 g of sodium hydroxide, 12.8 ml of water and 50 ml of ethanol was refluxed for 13 hours and then concentrated. Water was added to the residue and the resulting mixture was extracted with ether. The ether layer was extracted with hydrochloric acid. The aqueous layer was made alkaline with potassium carbonate and extracted with ethyl acetate. The extract was washed with water, dried and concentrated to give 5.05 g of pale brown crystals, mp 86°~88° C. The crystals were converted to the hydrochloride in the usual manner and then recrystallized from ethanol to give pale yellow prisms, mp 199°~200° C.

Analysis for $C_{18}H_{21}NS.HCl$: Calculated C, 67.58; H, 6.93; N, 4.38 Found C, 67.55; H, 6.79; N, 4.34

The compounds of References 28 to 38 were prepared in the same manner described in References 26 and 27.

Reference 28

(±)-4-[(2-Chlorophenyl)phenylmethoxy]piperidine hydrochloride

Colorless crystals, mp 157°~160° C. (EtOH-Et$_2$O).
Analysis for $C_{18}H_{20}ClNO.HCl$: Calculated C, 63.91; H, 6.26; N, 4.14 Found C, 63.69; H, 6.21; N, 4.12

Reference 29

(±)-4-[(3-Chlorophenyl)phenylmethoxy]piperidine fumarate

Colorless crystals, mp 159°~160° C. (MeOH-Et$_2$O).
Analysis for $C_{18}H_{20}ClNO.C_4H_4O_4$: Calculated C, 63.23; H, 5.79; N, 3.35 Found C, 63.16; H, 5.70; N, 3.33

Reference 30

(±)-4-[4-Chlorophenyl)phenylmethoxy]piperidine maleate

Colorless prisms, mp 159°~161° C. (EtOH).
Analysis for $C_{18}H_{20}ClNO.C_4H_4O_4$: Calculated C, 63.23; H, 5.79; N, 3.35 Found C, 63.07; H, 5.89; N, 3.39

Reference 31

(±)-4-[(4-Methylphenyl)phenylmethoxy]piperidine fumarate

Colorless needles, mp. 188°~189° C. (EtOH).
Analysis for $C_{19}H_{23}NO.C_4H_4O_4$: Calculated C, 69.50; H, 6.85; N, 3.52 Found C, 69.34; H, 7.02; N, 3.57

Reference 32

(±)-4-[(4-Methoxyphenyl)phenylmethoxy]piperidine fumarate

Colorless crystals, mp 152°~153° C. (EtOH-Et$_2$O).
Analysis for $C_{19}H_{23}NO_2.C_4H_4O_4.\frac{1}{4}H_2O$: Calculated C, 66.09; H, 6.63; N, 3.35 Found C, 66.06; H, 6.45; N, 3.42

Reference 33

(±)-4-[(4-Ethylphenyl)phenylmethoxy]piperidine fumarate

Colorless crystals, mp 127°~129° C. (EtOH-Et$_2$O).
Analysis for $C_{20}H_{25}NO.C_4H_4O_4$: Calculated C, 70.05; H, 7.10; N, 3.40 Found C, 70.33; H, 7.10; N, 3.43

Reference 34

(±)-4-[(4-n-Propylphenyl)phenylmethoxy]piperidine fumarate

Colorless needles, mp 142°~143.5° C. (EtOH-Et$_2$O).
Analysis for $C_{21}H_{27}NO.C_4H_4O_4$: Calculated C, 70.57; H, 7.34; N, 3.29 Found C, 70.62; H, 7.44; N, 3.32

Reference 35

(±)-4-[(4-n-Butylphenyl)phenylmethoxy]piperidine fumarate

Colorless pillars, mp 183°~184° C. (MeOH-Et$_2$O).
Analysis for $C_{22}H_{29}NO.\frac{1}{2}C_4H_4O_4$: Calculated C, 75.56; H, 8.19; N, 3.67 Found C, 75.39; H, 8.26; N, 3.56

Reference 36

(±)-4-[(4-tert-Butylphenyl)phenylmethoxy]piperidine fumarate

Colorless crystals, mp 163°~166° C. (EtOH-Et$_2$O).
Analysis for $C_{22}H_{29}NO.C_4H_4O_4$: Calculated C, 71.05; H, 7.57; N, 3.19 Found C, 70.99; H, 7.52; N, 3.23

Reference 37

4-[Bis(4-methylphenyl)methoxy]piperidine fumarate

Colorless needles, mp 164°~168° C. (MeOH).
Analysis for $C_{20}H_{25}NO.C_4H_4O_4$: Calculated C, 70.05; H, 7.10; N, 3.40 Found C, 69.93; H, 7.16; N, 3.31

Reference 38

(±)-4-[(4-Ethoxyphenyl)phenylmethoxy]piperidine fumarate

Colorless prisms, mp 112°~115° C. (EtOH).
Analysis for $C_{20}H_{25}NO.C_4H_4O_4$: Calculated C, 67.43; H, 6.84 N, 3.28 Found C, 67.24; H, 6.85; N, 3.33

Reference 39

(+)- and (−)-4-[(4-Methylphenyl)phenylmethoxy]piperidine (+)-Dibenzoyl-D-tartaric acid (19.3 g) was added to a solution of 25.3 g of (±)-4-[(4-methylphenyl)phenylmethoxy]-piperidine in methanol. The precipitate was collected by filtration to give 15.8 g of the crude (+)-dibenzoyl-D-tartarate. The mother liquor was concentrated and the residue obtained was converted to the free base in the usual manner. (−)-Dibenzoyl-L-tartaric acid (8.28 g) was added to the solution of the free base in methanol. The precipitate was collected by filtration to give 16.8 g of the crude (−)-dibenzoyl-L-tartarate. The crude (+)-dibenzoyl-D-tartarate was recrystallized from methanol to give 6.72 g of the pure (+)-dibenzoyl-D-tartarate as colorless needles, mp 166.5°~167° C. The needles were converted to the free base in the usual manner to give 3.73 g of (+)-4-[(4-methylphenyl)phenylmethoxy]piperidine as colorless liquid [specific rotation $[\alpha]_D^{20}+13.3°$ (c=0.5, CHCl$_3$), optical purity 96% ee]. The free base was converted to the fumarate in the usual manner, and the fumarate was recrystallized from ethanol to give colorless needles, mp 173°~174° C.

specific rotation $[\alpha]_D^{20}+10.2°$ (c=0.5, MeOH).

Analysis for $C_{19}H_{23}NO.C_4H_4O_4$: Calculated C, 69.50; H, 6.85; N, 3.52 Found C, 69.53; H, 6.93; N, 3.56

The crude (−)-dibenzoyl-L-tartarate was recrystallized from methanol to give 9.37 g of the pure (−)-dibenzoyl-L-tartarate as colorless needles, mp 169° C. The needles were converted to the free base in the usual manner to give 5.16 g of (−)-4-[(4-methylphenyl)-phenylmethoxy]piperidine as a colorless liquid [specific rotation $[\alpha]_D^{20}-13.4°$ (c=0.5, CHCl$_3$), optical purity 96% ee]. The free base was converted to the fumarate in the usual manner, and the fumarate was recrystallized from ethanol to give colorless needles, mp 173.5°~175° C.

specific rotation $[\alpha]_D^{20}-10.1°$ (c=0.5, MeOH).

Analysis for $C_{19}H_{23}NO.C_4H_4O_4$: Calculated C, 69.50; H, 6.85; N, 3.52 Found C, 69.62; H, 6.95; N, 3.60

EXAMPLE 1

(±)-Methyl 4-[(4-methylphenyl)phenylmethoxy]-1-piperidinecaproate hydrochloride

A mixture of 7.00 g of (±)-4-[(4-methylphenyl)-phenylmethoxy]-piperidine, 6.25 g of methyl 6-bromocaproate, 3.44 g of potassium carbonate and 35 ml of N,N-dimethylformamide was stirred at 70° C. for 3.5 hours. After cooling, water was added to the reaction mixture and the resulting mixture was extracted with ether. The ether layer was extracted with hydrochloric acid. The aqueous layer was made alkaline with potassium carbonate and extracted with ether. The extract was washed with water, dried and concentrated to give 8.96 g of yellow liquid. The yellow liquid was converted to the hydrochloride in the usual manner to give 8.29 g of pale orange crystals, which were then recrystallized from ethyl acetate to give colorless needles. mp 126°~129° C.

Analysis for $C_{26}H_{35}NO_3 \cdot HCl$: Calculated C, 70.01; H, 8.14; N, 3.14 Found C, 69.78; H, 8.13; N, 3.14

EXAMPLE 2

Ethyl 4-(diphenylmethoxy)-1-piperidinepropionate hydrochloride

A mixture of 5.34 g of 4-(diphenylmethoxy)piperidine, 3.98 g of ethyl 3-bromopropionate, 2.76 g of potassium carbonate and 30 ml of N,N-dimethylformamide was stirred at 70° C. for 3 hours. After cooling, water was added to the reaction mixture and the resulting mixture was extracted with ethyl acetate. The extract was washed with water, dried and concentrated to give 5.90 g of pale yellow liquid. The yellow liquid was converted to the hydrochloride in the usual manner, and the hydrochloride was then recrystallized from ethanol to give colorless plates, mp 176°~178° C.

Analysis for $C_{23}H_{29}NO_3 \cdot HCl$: Calculated C, 68.39; H, 7.49; N, 3.47 Found C, 68.29; H, 7.33; N, 3.45

EXAMPLE 3

Ethyl 4-[bis(4-methylphenyl)methoxy]-1-piperidinepropionate hydrochloride

A mixture of 3.25 g of 4-[bis(4-methylphenyl)methoxy]-piperidine, 1.43 g of ethyl acrylate and 20 ml of ethanol was refluxed for 2 hours and then concentrated. The residue was dissolved in ether and made acidic with ethanolic hydrogen chloride give 4.23 g of colorless crystals. The crystals were recrystallized from a mixture of acetone and ether to give colorless needles, mp 153°~156° C.

Analysis for $C_{25}H_{33}NO_3 \cdot HCl$: Calculated C, 69.51; H, 7.93; N, 3.24 Found C, 69.39; H, 7.96; N, 3.25

EXAMPLE 4

Ethyl 4-(diphenylmethylthio)-1-piperidinepropionate hydrochloride

A mixture of 1.70 g of 4-(diphenylmethylthio)piperidine, 1.30 g of ethyl 3-bromopropionate, 0.83 g of potassium carbonate and 10 ml of N,N-dimethylformamide was stirred at 70° C. for 3 hours. After cooling, water was added to the reaction mixture and the resulting mixture was extracted with ether. The ether layer was extracted with hydrochloric acid. The aqueous layer was made alkaline with potassium carbonate and extracted with ether. The extract was washed with water, dried and concentrated to give 1.98 g of pale yellowish brown liquid. The brown liquid was converted to the hydrochloride and then recrystallized from a mixture of ethanol and ether to give colorless crystals, mp 149°~150° C.

Analysis for $C_{23}H_{29}NO_2S \cdot HCl$: Calculated C, 65.77; H, 7.20; N, 3.33 Found C, 65.72; H, 7.06; N, 3.36

EXAMPLE 5

(±)-Methyl 2-[4-[(4-fluorophenyl)phenylmethoxy]piperidino]-ethoxyacetate

A mixture of 4.46 g of (±)-[(4-fluorophenyl)-phenylmethoxy]-piperidine, 2.75 g of methyl 2-chloroethoxyacetate, 2.07 g of potassium carbonate and 45 ml of N,N-dimethylformamide was stirred at 70° C. for 22 hours. After cooling, water was added to the reaction mixture and extracted with ether. The extract was washed with water, dried and evaporated. The residue was purified by column chromatography on silica gel [eluent: chloroform-methanol (50:1)] to give 4.40 g of yellowish orange liquid.

Mass spectrum m/z: 401 (M+).

IR spectrum $\nu$(liq) cm$^{-1}$: 1758 (COO—).

NMR spectrum $\delta$(CDCl$_3$) ppm: 1.60–2.00 (4H, m), 2.00–3.00 (4H, m), 2.60 (2H, t, J=5.5 Hz), 3.20–3.55 (1H, m), 3.66 (2H, t, J=5.5 Hz), 3.73 (3H, s), 4.11 (2H, s), 5.48 (1H, s), 6.97 (2H, t, J=9 Hz), 7.15–7.45 (7H, m).

The compounds of Example 6 to 63 were prepared in the same manner described in Example 1 to 5.

EXAMPLE 6

(±)-Ethyl 4-[(4-methylphenyl)phenylmethoxy]-1-piperidineacetate

Pale yellow liquid.

Mass spectrum m/z: 367 (M+).

IR spectrum $\nu$(liq) cm$^{-1}$: 1746 (COO—).

NMR spectrum $\delta$(CDCl$_3$) ppm: 1.25 (3H, t, J=7 Hz), 1.66–2.06 (4H, m), 2.06–2.96 (4H, m), 2.31 (3H, s), 3.19 (2H, s), 3.28–3.62 (1H, m), 4.16 (2H, q, J=7 Hz), 5.47 (1H, s), 7.00–7.42 (9H, m).

EXAMPLE 7

(±)-Ethyl 4-[(4-methylphenyl)phenylmethoxy]-1-piperidinepropionate fume

Colorless crystals, mp 101°~104° C. (EtOH-Et$_2$O).

Analysis for $C_{24}H_{31}NO_3 \cdot C_4H_4O_4$: Calculated C, 67.59; H, 7.09; N, 2.81 Found C, 67.29; H, 7.15; N, 2.83

EXAMPLE 8

(±)-Ethyl 4-[(4-methylphenyl)phenylmethoxy]-1-piperidinebutyrate

Yellow liquid.

Mass spectrum m/z: 395 (M+).

IR spectrum $\nu$(liq) cm$^{-1}$: 1736 (COO—).

NMR spectrum $\delta$(CDCl$_3$) ppm: 1.24 (3H, t, J=7 Hz), 1.40–3.00 (14H,m), 2.31 (3H, s), 3.20–3.60 (1H, m), 4.11 (2H, q, J=7 Hz), 5.48 (1H, s), 7.00–7.50 (9H, m).

EXAMPLE 9

(±)-Ethyl 4-[(4-methylphenyl)phenylmethoxy]-1-piperidinevalerate fumarate

Colorless needles, mp 116°~117° C. (AcOEt).
Analysis for $C_{26}H_{35}NO_3 \cdot C_4H_4O_4$: Calculated C, 68.55; H, 7.48; N, 2.66 Found C, 68.36; H, 7.35; N, 2.59

EXAMPLE 10

(±)-Methyl 4-[(4-methylphenyl)phenylmethoxy]-1-piperidineheptanoate fumarate

Colorless crystals, mp 45°~48° C. (AcOEt).
Analysis for $C_{27}H_{37}NO_3 \cdot C_4H_4O_4$: Calculated C, 68.99; H, 7.66; N, 2.60 Found C, 68.77; H, 7.72; N, 2.63

EXAMPLE 11

(±)-Methyl 4-[(4-methylphenyl)phenylmethoxy]-1-piperidineoctanoate fumarate

Colorless crystals, mp 44°~48° C. (AcOEt).
Analysis for $C_{28}H_{39}NO_3 \cdot C_4H_4O_4$: Calculated C, 69.42; H, 7.83; N, 2.53 Found C, 69.20; H, 7.97; N, 2.61

EXAMPLE 12

(±)-Methyl 2-[4-[(4-methylphenyl)phenylmethoxy]piperidino]ethoxyacetate

Pale yellow liquid.
Mass spectrum m/z: 397 (M+).
IR spectrum $\nu$(liq) cm$^{-1}$: 1758 (COO—).
NMR spectrum $\delta$(CDCl$_3$) ppm: 1.64-2.04 (4H, m), 2.04-2.96 (4H, m), 2.31 (3H, s), 2.60 (2H, t, J=5.5 Hz), 3.30-3.56 (1H, m), 3.66 (2H, t, J=5.5 Hz) 3.73 (3H, s), 4.11 (2H, s), 5.47 (1H, s), 7.00-7.40 (9H, m).

EXAMPLE 13

(±)-Ethyl 4-[(4-ethylphenyl)phenylmethoxy]-1-piperidinepropionate hydrochloride

Colorless prisms, mp 142°~145° C. (AcOEt).
Analysis for $C_{25}H_{33}NO_3 \cdot HCl$: Calculated C, 69.51; H, 7.93; N, 3.24 Found C, 69.23; H, 7.91; N, 3.33

EXAMPLE 14

(±)-Methyl 4-[(4-ethylphenyl)phenylmethoxy]-1-piperidinecaproate

Yellow liquid.
Mass spectrum m/z: 423 (M+).
IR spectrum $\nu$(liq) cm$^{-1}$: 1738 (COO—).
NMR spectrum $\delta$(CDCl$_3$) ppm: 1.09-2.97 (18H, m), 1.21 (3H, t, J=7.5 Hz), 2.62 (2H, q, J=7.5 Hz), 3.28-3.60 (1H, m), 3.65 (3H, s), 5.48 (1H, s), 7.03-7.50 (9H, m).

EXAMPLE 15

(±)-Ethyl 4-[(4-n-propylphenyl)phenylmethoxy]-1-piperidinepropionate hydrochloride Colorless needles, mp 154°~156° C. (AcOEt).
Analysis for $C_{26}H_{35}NO_3 \cdot HCl$: Calculated C, 70.01; H, 8.14; N, 3.14 Found C, 70.00; H, 8.13; N, 3.21

EXAMPLE 16

(±)-Methyl 4-[(4-n-propylphenyl)phenylmethoxy]-1-piperidinecaproate fumarate

Colorless crystals, mp 108°~110° C. (AcOEt).
Analysis for $C_{28}H_{39}NO_3 \cdot C_4H_4O_4$: Calculated C, 69.42; H, 7.83; N, 2.53 Found C, 69.23; H, 7.79; N, 2.58

EXAMPLE 17

(±)-Ethyl 4-[(4-n-butylphenyl)phenylmethoxy]-1-piperidinepropionate hydrochloride Colorless needles, mp 167°~170° C. (AcOEt).
Analysis for $C_{27}H_{37}NO_3 \cdot HCl$: Calculated C, 70.49; H, 8.33; N, 3.04 Found C, 70.49; H, 8.27; N, 3.08

EXAMPLE 18

(±)-Methyl 4-[(4-n-butylphenyl)phenylmethoxy]-1-piperidinecaproate

Pale yellow liquid.
Mass spectrum m/z: 451 (M+).
IR spectrum $\nu$(liq) cm$^{-1}$: 1740 (COO—).
NMR spectrum $\delta$(CDCl$_3$) ppm: 0.91 (3H, t, J=7 Hz), 1.12-3.00 (24H, m), 3.30-3.58 (1H, m), 3.65 (3H, s), 5.48 (1H, s), 7.04-7.44 (9H, m).

EXAMPLE 19

(±)-Ethyl 4-[(4-tert-butylphenyl)phenylmethoxy]-1-piperidinepropionate hydrochloride Colorless flakes, mp 138°~140.5° C. (AcOEt).
Analysis for $C_{27}H_{37}NO_3 \cdot HCl$: Calculated C, 70.49; H, 8.33; N, 3.04 Found C, 70.47; H, 8.19; N, 3.11

EXAMPLE 20

(±)-Methyl 4-[(4-tert-butylphenyl)phenylmethoxy]-1-piperidinecaproate fumarate

Colorless crystals, mp 108°~110° C. (AcOEt).
Analysis for $C_{29}H_{41}NO_3 \cdot C_4H_4O_4$: Calculated C, 69.82; H, 7.99; N, 2.47 Found C, 69.65; H, 7.94; N, 2.39

EXAMPLE 21

Methyl 4-[bis(4-methylphenyl)methoxy]-1-piperidinecaproate fumarate

Colorless crystals, mp 50°~53° C. (AcOEt).
Analysis for $C_{27}H_{37}NO_3 \cdot C_4H_4O_4$: Calculated C, 68.99; H, 7.66; N, 2.60 Found C, 68.73; H, 7.69; N, 2.59

EXAMPLE 22

(±)-Ethyl 4-[(4-methoxyphenyl)phenylmethoxy]-1-piperidineacetate maleate

Colorless needles, mp 109°~112° C. (Me$_2$CO-Et$_2$O).
Analysis for $C_{23}H_{29}NO_4 \cdot C_4H_4O_4$: Calculated C, 64.92; H, 6.66; N, 2.80 Found C, 64.87; H, 6.64; N, 2.88

EXAMPLE 23

(±)-Ethyl 4-[(4-methoxyphenyl)phenylmethoxy]-1-piperidinepropionate fumarate

Colorless crystals, mp 109°~111° C. (EtOH-Et$_2$O).
Analysis for C$_{24}$H$_{31}$NO$_4$·C$_4$H$_4$O$_4$: Calculated C, 65.48; H, 6.87; N, 2.73 Found C, 65.37; H, 6.82; N, 2.64

EXAMPLE 24

(±)-Ethyl 4-[(4-methoxyphenyl)phenylmethoxy]-1-piperidinebutyrate fumarate

Colorless crystals, mp 127°~130° C. (EtOH-Et$_2$O).
Analysis for C$_{25}$H$_{33}$NO$_4$·C$_4$H$_4$O$_4$: Calculated C, 66.02; H, 7.07; N, 2.65 Found C, 65.82; H, 7.12; N, 2.63

EXAMPLE 25

(±)-Ethyl 4-[(4-methoxyphenyl)phenylmethoxy]-1-piperidinevalerate fumarate

Pale brown prisms, mp 117°~119° C. (Me$_2$CO-Et$_2$O).
Analysis for C$_{26}$H$_{35}$NO$_4$·C$_4$H$_4$O$_4$: Calculated C, 66.53; H, 7.26; N, 2.59 Found C, 66.41; H, 7.13; N, 2.47

EXAMPLE 26

(±)-Methyl 4-[(4-methoxyphenyl)phenylmethoxy]-1-piperidinecaproate fumarate

Colorless flakes, mp 95°~97° C. (Me$_2$CO-Et$_2$O).
Analysis for C$_{26}$H$_{35}$NO$_4$·C$_4$H$_4$O$_4$: Calculated C, 66.53; H, 7.26; N, 2.59 Found C, 66.42; H, 7.01; N, 2.60

EXAMPLE 27

(±)-Methyl 4-[(4-methoxyphenyl)phenylmethoxy]-1-piperidineheptanoate fumarate

Colorless crystals, mp 97°~101° C. (AcOEt).
Analysis for C$_{27}$H$_{37}$NO$_4$·C$_4$H$_4$O$_4$: Calculated C, 67.01; H, 7.44; N, 2.52 Found C, 66.97; H, 7.39; N, 2.61

EXAMPLE 28

(±)-Methyl 4-[(4-methoxyphenyl)phenylmethoxy]-1-piperidineoctanoate fumarate

Colorless crystals, mp 104°~106° C. (AcOEt).
Analysis for C$_{28}$H$_{39}$NO$_4$·C$_4$H$_4$O$_4$: Calculated C, 67.47; H, 7.61; N, 2.46 Found C, 67.24; H, 7.77; N, 2.56

EXAMPLE 29

(±)-Methyl 2-[4-[(4-methoxyphenyl)phenylmethoxy]piperidino]ethoxyacetate

Pale yellow liquid.
Mass spectrum m/z: 413 (M+).
IR spectrum ν(liq) cm$^{-1}$: 1756 (COO—).
NMR spectrum δ(CDCl$_3$) ppm: 1.60–2.08 (4H, m), 2.08–3.00 (4H, m), 2.61 (2H, t, J=5.5 Hz), 3.30–3.56 (1H, m), 3.67 (2H, t, J=5.5 Hz), 3.73 (3H, s), 3.77 (3H, s), 4.11 (2H, s), 5.47 (1H, s), 6.83 (2H, d, J=9 Hz), 7.23 (2H, d, J=9 Hz), 7.08–7.44 (5H, m).

EXAMPLE 30

(±)-Ethyl 4-[(4-ethoxyphenyl)phenylmethoxy]-1-piperidinepropionate fumarate

Colorless crystals, mp 149°~150.5° C. (AcOEt).
Analysis for C$_{25}$H$_{33}$NO$_4$·C$_4$H$_4$O$_4$: Calculated C, 66.02; H, 7.07; N, 2.65 Found C, 65.89; H, 7.02; N, 2.65

EXAMPLE 31

(±)-Methyl 4-[(4-ethoxyphenyl)phenylmethoxy]-1-piperidinecaproate fumarate

Colorless crystals, mp 128°~131° C. (AcOEt).
Analysis for C$_{27}$H$_{37}$NO$_4$·C$_4$H$_4$O$_4$: Calculated C, 67.01; H, 7.44; N, 2.52 Found C, 66.98; H, 7.52; N, 2.52

EXAMPLE 32

Ethyl 4-(diphenylmethoxy)-1-piperidineacetate

Pale yellow liquid.
Mass spectrum m/z: 353 (M+).
IR spectrum ν(liq) cm$^{-1}$: 1748 (COO—).
NMR spectrum δ(CDCl$_3$) ppm: 1.25 (3H, t, J=7 Hz), 1.56–2.10 (4H, m), 2.20–3.00 (4H, m), 3.20 (2H, s), 3.30–3.64 (1H, m), 4.17 (2H, q, J=7 Hz), 5.50 (1H, s), 7.08–7.64 (10H, m).

EXAMPLE 33

(±)-Ethyl 4-(diphenylmethoxy)-α-methyl-1-piperidineacetate

Pale yellow liquid.
Mass spectrum m/z: 367 (M+).
IR spectrum ν(liq) cm$^{-1}$: 1730 (COO—).
NMR spectrum δ(CDCl$_3$) ppm: 1.24 (3H, t, J=7 Hz), 1.27 (3H, d, J=7 Hz), 1.50–2.10 (4H, m), 2.15–3.05 (4H, m), 3.27 (1H, q, J=7 Hz), 3.15–3.65 (1H, m), 4.14 (2H, q, J=7 Hz), 5.50 (1H, s), 7.05–7.45 (10H, m).

EXAMPLE 34

Ethyl 4-(diphenylmethoxy)-1-piperidinevalerate hydrochloride

Colorless flakes, mp 137°~139° C. (AcOEt).
Analysis for C$_{25}$H$_{33}$NO$_3$·HCl: Calculated C, 69.51; H, 7.93; N, 3.24 Found C, 69.50; H, 7.86; N, 3.33

EXAMPLE 35

Methyl 4-(diphenylmethoxy)-1-piperidinecaproate hydrochloride

Colorless needles, mp 142.5°~143.5° C. (H$_2$O).
Analysis for C$_{25}$H$_{33}$NO$_3$·HCl: Calculated C, 69.51; H, 7.93; N, 3.24 Found C, 69.31; H, 7.82; N, 3.31

EXAMPLE 36

Methyl 4-(diphenylmethoxy)-1-piperidineheptanoate hydrochloride

Colorless crystals, mp 105°~108° C. (AcOEt).
Analysis for C$_{26}$H$_{35}$NO$_3$·HCl: Calculated C, 70.01; H, 8.14; N, 3.14 Found C, 69.95; H, 8.10; N, 3.16

EXAMPLE 37

Methyl 4-(diphenylmethoxy)-1-piperidineoctanoate hydrochloride

Colorless needles, mp 115°~118° C. (AcOEt).

Analysis for $C_{27}H_{37}NO_3 \cdot HCl$: Calculated C, 70.49; H, 8.33; N, 3.04 Found C, 70.31; H, 8.50; N, 3.06

EXAMPLE 38

Methyl 2-[4-(diphenylmethoxy)piperidino]ethoxyacetate

Colorless liquid.
Mass spectrum m/z: 383 (M+).
IR spectrum $\nu$(liq) cm$^{-1}$: 1756 (COO—).
NMR spectrum $\delta$(CDCl$_3$) ppm: 1.50–2.97 (8H, m), 2.61 (2H, t, J=6 Hz), 3.30–3.60 (1H, m), 3.67(2H, t, J=6 Hz), 3.73 (3H, s), 4.11 (2H, s), 5.50 (1H, s), 7.29 (10H, s-like).

EXAMPLE 39

($\pm$)-Ethyl 4-[(4-chlorophenyl)phenylmethoxy]-1-piperidineacetate hydrochloride Colorless needles, mp 166°~167° C. (EtOH-Et$_2$O).
Analysis for $C_{22}H_{26}ClNO_3 \cdot HCl$: Calculated C, 62.27; H, 6.41; N, 3.30 Found C, 62.02; H, 6.36; N, 3.22

EXAMPLE 40

($\pm$)-Ethyl 4-[(4-chlorophenyl)phenylmethoxy]-1-piperidinepropionate hydrochloride Colorless crystals, mp 187°~189° C. (EtOH-Et$_2$O).
Analysis for $C_{23}H_{28}ClNO_3 \cdot HCl$: Calculated C, 63.01; H, 6.67; N, 3.20 Found C, 62.77; H, 6.63; N, 3.24

EXAMPLE 41

($\pm$)-Ethyl 4-[(4-chlorophenyl)phenylmethoxy]-1-piperidinevalerate fumarate

Colorless needles, mp 125°~126° C. (H$_2$O).
Analysis for $C_{25}H_{32}ClNO_3 \cdot C_4H_4O_4$: Calculated C, 63.79; H, 6.65; N, 2.57 Found C, 63.78; H, 6.54; N, 2.59

EXAMPLE 42

($\pm$)-Methyl 4-[(4-chlorophenyl)phenylmethoxy]-1-piperidinecaproate

Yellow liquid.
Mass spectrum m/z: 429, 431 (3:1, M+).
IR spectrum $\nu$(liq) cm$^{-1}$: 1738 (COO—).
NMR spectrum $\delta$(CDCl$_3$) ppm: 1.20–1.92 (10H, m), 1.96–2.88 (6H, m), 2.30 (2H, t, J=7 Hz), 3.26–3.54 (1H, m), 3.64 (3H, s), 5.46 (1H, s), 7.16–7.40 (9H, m).

EXAMPLE 43

($\pm$)-Methyl 4-[(4-chlorophenyl)phenylmethoxy]-1-piperidineheptanoate hydrochloride Colorless crystals, mp 116°~119° C. (AcOEt).
Analysis for $C_{26}H_{34}ClNO_3 \cdot HCl$: Calculated C, 65.00; H, 7.34; N, 2.92 Found C, 64.93; H, 7.26; N, 2.95

EXAMPLE 44

($\pm$)-Methyl 4-[(4-chlorophenyl)phenylmethoxy]-1-piperidineoctanoate fumarate

Colorless crystals, mp 95°~97° C. (AcOEt-Et$_2$O).
Analysis for $C_{27}H_{36}ClNO_3 \cdot C_4H_4O_4$: Calculated C, 64.85; H, 7.02; N, 2.44 Found C, 64.70; H, 7.02; N, 2.37

EXAMPLE 45

($\pm$)-Methyl 2-[4-[(4-chlorophenyl)phenylmethoxy]piperidino]ethoxyacetate

Pale yellow liquid.
Mass spectrum m/z: 417, 419 (3:1, M+).
IR spectrum $\nu$(liq) cm$^{-1}$: 1758 (COO—).
NMR spectrum $\delta$(CDCl$_3$) ppm: 1.60–1.96 (4H, m), 2.04–2.36 (2H, m), 2.60 (2H, t, J=5.5 Hz), 2.66–2.96 (2H, m), 3.26–3.60 (1H, m), 3.66 (2H, t, J=5.5 Hz), 3.73 (3H, s), 4.11 (2H, s), 5.47 (1H, s), 7.10–7.44 (9H, m).

EXAMPLE 46

($\pm$)-Ethyl 4-[(3-chlorophenyl)phenylmethoxy]-1-piperidinepropionate hydrochloride Colorless crystals, mp 170°~172° C. (H$_2$O).
Analysis for $C_{23}H_{28}ClNO_3 \cdot HCl$: Calculated C, 63.01; H, 6.67; N, 3.20 Found C, 62.80; H, 6.42; N, 3.15

EXAMPLE 47

($\pm$)-Ethyl 4-[(3-chlorophenyl)phenylmethoxy]-1-piperidinebutyrate

Pale yellow liquid.
Mass spectrum m/z: 415, 417 (3:1, M+).
IR spectrum $\nu$(liq) cm$^{-1}$: 1734 (COO—).
NMR spectrum $\delta$(CDCl$_3$) ppm: 1.25 (3H, t, J=7 Hz), 1.50–3.00 (14H, m), 3.20–3.60 (1H, m), 4.12 (2H, q, J=7 Hz), 5.46 (1H, s), 7.10–7.50 (9H, m).

EXAMPLE 48

($\pm$)-Ethyl 4-[(2-chlorophenyl)phenylmethoxy]-1-piperidinepropionate hydrochloride Colorless crystals, mp 144°~146° C. (Me$_2$CO-Et$_2$O).
Analysis for $C_{23}H_{28}ClNO_3 \cdot HCl$: Calculated C, 63.01; H, 6.67; N, 3.20 Found C, 62.93; H, 6.75; N, 3.12

EXAMPLE 49

($\pm$)-Ethyl 4-[(2-chlorophenyl)phenylmethoxy]-1-piperidinebutyrate

Yellowish orange liquid.
Mass spectrum m/z: 415, 417 (3:1, M+).
IR spectrum $\nu$(liq) cm$^{-1}$: 1736 (COO—).
NMR spectrum $\delta$(CDCl$_3$) ppm: 1.24 (3H, t, J=7 Hz), 1.40–2.95 (14H, m), 3.20–3.60 (1H, m), 4.11 (2H, q, J=7 Hz), 5.97 (1H, s), 7.00–7.70 (9H, m).

EXAMPLE 50

($\pm$)-Ethyl 4-[(4-fluorophenyl)phenylmethoxy]-1-piperidineacetate hydrochloride Colorless needles, mp 167°~170° C. (EtOH-Et$_2$O).
Analysis for $C_{22}H_{26}FNO_3 \cdot HCl$: Calculated C, 64.78; H, 6.67; N, 3.43 Found C, 64.73; H, 6.58; N, 3.30

EXAMPLE 51

($\pm$)-Ethyl 4-[(4-fluorophenyl)phenylmethoxy]-1-piperidinepropionate hydrochloride Colorless needles, mp 200°~201° C. (EtOH-Et$_2$O).

Analysis for $C_{23}H_{28}FNO_3 \cdot HCl$: Calculated C, 65.47; H, 6.93; N, 3.32 Found C, 65.17; H, 6.87; N, 3.34

EXAMPLE 52

(±)-Ethyl 4-[(4-fluorophenyl)phenylmethoxy]-1-piperidinebutyrate hydrochloride

Colorless needles, mp 128°~131° C. (AcOEt).
Analysis for $C_{24}H_{30}FNO_3 \cdot HCl$: Calculated C, 66.12; H, 7.17; N, 3.21 Found C, 66.07; H, 7.03; N, 3.15

EXAMPLE 53

(±)-Ethyl 4-[(4-fluorophenyl)phenylmethoxy]-1-piperidinevalerate hydrochloride

Pale brown crystals, mp 122°~123° C. (AcOEt-Et$_2$O).
Analysis for $C_{25}H_{32}FNO_3 \cdot HCl$: Calculated C, 66.73; H, 7.39; N, 3.11 Found C, 66.44; H, 7.37; N, 3.13

EXAMPLE 54

(±)-Methyl 4-[(4-fluorophenyl)phenylmethoxy]-1-piperidinecaproate hydrochloride

Pale brown needles, mp 139°~142° C. (AcOEt)
Analysis for $C_{25}H_{32}FNO_3 \cdot HCl$: Calculated C, 66.73; H, 7.39; N, 3.11 Found C, 66.74; H, 7.33; N, 3.09

EXAMPLE 55

Ethyl 4-[bis(4-fluorophenyl)methoxy]-1-piperidineacetate hydrochloride

Colorless needless, mp 160°~161.5° C. (EtOH-Et$_2$O).
Analysis for $C_{22}H_{25}F_2NO_3 \cdot HCl$: Calculated C, 62.04; H, 6.15; N, 3.29 Found C, 62.01; H, 6.11; N, 3.37

EXAMPLE 56

Ethyl 4-[bis(4-fluorophenyl)methoxy]-1-piperidinepropionate hydrochloride

Colorless crystals, mp 192°~197° C. (Me$_2$CO)
Analysis for $C_{23}H_{27}F_2NO_3 \cdot HCl$: Calculated C, 62.79; H, 6.42; N, 3.18 Found C, 62.75; H, 6.36; N, 3.18

EXAMPLE 57

Ethyl 4-[bis(4-fluorophenyl)methoxy]-1-piperidinevalerate

Yellow liquid.
Mass spectrum m/z: 431 (M+).
IR spectrum $\nu$ (liq) cm$^{-1}$: 1734 (COO—).
NMR spectrum $\delta$(CDCl$_3$) ppm: 1.25 (3H, t, J=7 Hz), 1.40-1.94 (8H, m), 1.98-2.92 (8H, m), 3.26-3.56 (1H, m), 4.12 (2H, q, J=7 Hz), 5.46 (1H, s), 6.99 (4H, t, J=8.5 Hz), 7.27 (4H, dd, J=8.5, 6 Hz).

EXAMPLE 58

Methyl 4-[bis(4-fluorophenyl)methoxy]-1-piperidinecaproate hydrochloride

Colorless needles, mp 143°~146° C. (Me$_2$CO-Et$_2$O).
Analysis for $C_{25}H_{31}F_2NO_3 \cdot HCl$: Calculated C, 64.16; H, 6.89; N, 2.99 Found C, 64.05; H, 6.92; N, 2.86

EXAMPLE 59

Methyl 2-[4-[bis(4-fluorophenyl)methoxy]piperidino]ethoxyacetate

Yellowish orange liquid.
Mass spectrum m/z: 419 (M+).
IR spectrum $\nu$(liq) cm$^{-1}$: 1754 (COO—).
NMR spectrum $\delta$(CDCl$_3$) ppm: 1.45-2.05 (4H, m), 2.05-3.00 (4H, m), 2.62 (2H, t, J=5.5 Hz), 3.20-3.60 (1H, m), 3.67 (2H, t, J=5.5 Hz), 3.74 (3H, s), 4.12 (2H, s), 5.46 (1H, s), 6.99 (4H, t, J=8.5 Hz), 7.27 (4H, dd, J=8.5, 5.5 Hz).

EXAMPLE 60

Ethyl 4-(diphenylmethylthio)-1-piperidinebutyrate

Pale yellow liquid.
Mass spectrum m/z: 397 (M+).
IR spectrum $\nu$(liq) cm$^{-1}$: 1734 (COO—).
NMR spectrum $\delta$(CDCl$_3$) ppm: 1.24 (3H, t, J=7 Hz), 1.40-2.20 (10H, m), 2.30 (2H, t, J=7 Hz), 2.40-3.00 (3H, m), 4.11 (2H, q, J=7 Hz), 5.21 (1H, s), 7.00-7.60 (10H, m).

EXAMPLE 61

Methyl 2-[4-(diphenylmethylthio)piperidino]ethoxyacetate

Pale yellow liquid.
Mass spectrum m/z: 399 (M+).
IR spectrum $\nu$(liq) cm$^{-1}$: 1758 (COO—).
NMR spectrum $\delta$(CDCl$_3$) ppm: 1.40-2.55 (7H, m), 2.58 (2H, t, J=5.5 Hz), 2.70-3.00 (2H, m), 3.65 (2H, t, J=5.5 Hz), 3.73 (3H, s), 4.10 (2H, s), 5.21 (1H, s), 7.15-7.55 (10H, m).

EXAMPLE 62

(+)-Methyl 4-[(4-methylphenyl)phenylmethoxy]-1-piperidinecaproate hydrochloride

Colorless needles, mp 142.5°-143.5° C. (AcOEt).
specific rotation $[\alpha]_D^{20}$+9.0° (c=0.5, MeOH).
Analysis for $C_{26}H_{35}NO_3 \cdot HCl$: Calculated C, 70.01; H, 8.14; N, 3.14 Found C, 69.80; H, 8.18; N, 3.27

EXAMPLE 63

(−)-Methyl 4-[(4-methylphenyl)phenylmethoxy]-1-piperidinecaproate hydrochloride

Colorless needles, mp 142.5°~143.5° C. (AcOEt).
specific rotation $[\alpha]_D^{20}$−9.1° (c=0.5, MeOH).
Analysis for $C_{26}H_{35}NO_3 \cdot HCl$: Calculated C, 70.01; H, 8.14; N, 3.14 Found C, 69.75; H, 8.18; N, 3.21

EXAMPLE 64

(±)-4-[(4-Methylphenyl)phenylmethoxy]-1-piperidinecaproic acid hydrochloride

A mixture of 8.29 g of (±)-methyl 4-[(4-methylphenyl)-phenylmethoxy]-1-piperidinecaproate hydrochloride in 40 ml of methanol and 28 ml of 2N sodium hydroxide aqueous solution was refluxed for 1 hour and concentrated. Water was added to the residue, made acidic with hydrochloric acid and extracted with chloroform. The extract was dried and concentrated. The residue was solidified by treatment with ethyl acetate and ether. The precipitate was collected by filtration to give 7.73 g of colorless crystals. The crystals were then recrystallized from a mixture of water and acetone to give 5.80 g of colorless prisms, mp 168°~170° C.

Analysis for $C_{25}H_{33}NO_3 \cdot HCl$: Calculated C, 69.51; H, 7.93; N, 3.24 Found C, 69.43; H, 8.07; N, 3.24

EXAMPLE 65

4-(Diphenylmethoxy)-1-piperidinepropionic acid hydrochloride

A mixture of 3.22 g of ethyl 4-(diphenylmethoxy)-1-piperidinepropionate hydrochloride in 30 ml of methanol and 12.0 ml of 2N sodium hydroxide aqueous solution was refluxed for 1 hour and concentrated. Water was added to the residue and made acidic with hydrochloric acid. The precipitate was collected by filtration and recrystallized from water to give 2.64 g of colorless needles, mp 183°~185° C.

Analysis for $C_{21}H_{25}NO_3 \cdot HCl \cdot \frac{1}{2}H_2O$: Calculated C, 65.53; H, 7.07; N, 3.64 Found C, 65.73; H, 6.87; N, 3.80

EXAMPLE 66

4-[Bis(4-methylphenyl)methoxy]-1-piperidinepropionic acid hydrochloride

A mixture of 3.55 g of ethyl 4-[bis(4-methylphenyl)-methoxy]-1-piperidinepropionate hydrochloride, 12.4 ml of 2N sodium hydroxide aqueous solution and 20 ml of methanol was refluxed for 1 hour and then concentrated. Water was added to the residue and made acidic with hydrochloric acid. The resulting precipitate was collected by filtration to give 3.29 g of colorless crystals. The crystals were recrystallized from water to give 2.63 g of colorless needles, mp 159°~162° C.

Analysis for $C_{23}H_{29}NO_3 \cdot HCl$: Calculated C, 68.39; H, 7.49; N, 3.47 Found C, 68.43; H, 7.49; N, 3.39

EXAMPLE 67

4-(Diphenylmethylthio)-1-piperidinepropionic acid hydrochloride

A mixture of 1.45 g of ethyl 4-(diphenylmethylthio)-1-piperidinepropionate in 15 ml of methanol and 5.7 ml of 2N sodium hydroxide aqueous solution was refluxed for 1 hour and concentrated. Water was added to the residue and made acidic with hydrochloric acid. The precipitate was collected by filtration and recrystallized from a mixture of ethanol and ether to give 1.04 g of colorless plates, mp 170°~172° C.

Analysis for $C_{21}H_{25}NO_2S \cdot HCl \cdot \frac{1}{2}H_2O$ Calculated C, 62.91; H, 6.79; N, 3.49 Found C, 63.03; H, 7.03; N, 3.31

EXAMPLE 68

(±)-2-[4-(4-Fluorophenyl)phenylmethoxy]-piperidino]ethoxyacetic acid

A mixture of 3.81 g of (±)-methyl 2-[4-[(4-fluorophenyl)-phenylmethoxy]piperidino]ethoxyacetate in 35 ml of methanol and 9.2 ml of 2N sodium hydroxide aqueous solution was refluxed for 2 hours and concentrated. Water was added to the residue, made acidic with hydrochloric acid and extracted with chloroform. The extract was dried and evaporated. The resulting residue was dissolved in chloroform and the chloroform solution was made alkaline by bubbling ammonia gas through the solution. The resulting precipitate was filtered off and the filtrate was concentrated to give 2.09 g of pale brown liquid.

Mass spectrum m/z: 387 (M+).
IR spectrum $\nu$(liq) $cm^{-1}$: 1606 (COO—)

NMR spectrum $\delta(CDCl_3)$ ppm: 1.73-2.40 (4H, m), 2.80-3.40 (6H, m), 3.53-3.93 (3H, m), 4.00 (2H, s), 5.43 (1H, s), 7.00 (2H, t, J=8.5 Hz), 7.15-7.50 (7H, m).

The compounds of Examples 69 to 126 were prepared in the same manner described in Examples 64 to 68.

EXAMPLE 69

(±)-4-[(4-Methylphenyl)phenylmethoxy]-1-piperidineacetic acid

Colorless needles, mp 73.5°~75° C. ($H_2O$).
Analysis for $C_{21}H_{25}NO_3 \cdot 2H_2O$: Calculated C, 67.18; H, 7.79; N, 3.73 Found C, 67.10; H, 7.51; N, 3.81

EXAMPLE 70

(±)-4-[(4-Methylphenyl)phenylmethoxy]-1-piperidinepropionic acid hydrochloride

Colorless crystals, mp 157°~159° C. (EtOH-$Et_2O$).
Analysis for $C_{22}H_{27}NO_3 \cdot HCl$: Calculated C, 67.77; H, 7.24; N, 3.59 Found C, 67.63; H, 6.99; N, 3.54

EXAMPLE 71

(±)-4-[(4-Methylphenyl)phenylmethoxy]-1-piperidinebutyric acid hydrochloride

Colorless crystals, mp 151°~153° C. (EtOH-$Et_2O$).
Analysis for $C_{23}H_{29}NO_3 \cdot HCl$: Calculated C, 68.39; H, 7.49; N, 3.47 Found C, 68.19; H, 7.33; N, 3.27

EXAMPLE 72

(±)-4-[(4-Methylphenyl)phenylmethoxy]-1-piperidinevaleric acid hydrochloride

Colorless prisms, mp 171.5°~173° C. (MeOH-$Et_2O$).
Analysis for $C_{24}H_{31}NO_3 \cdot HCl$: Calculated C, 68.97; H, 7.72; N, 3.35 Found C, 68.81; H, 7.49; N, 3.29

EXAMPLE 73

(±)-4-[(4-Methylphenyl)phenylmethoxy]-1-piperidineheptanoic acid hydrochloride

Colorless crystals, mp 147°~150° C. (EtOH-AcOEt).
Analysis for $C_{26}H_{35}NO_3 \cdot HCl$: Calculated C, 70.01; H, 8.14; N, 3.14 Found C, 69.83; H, 8.04; N, 3.13

EXAMPLE 74

(±)-4-[(4-Methylphenyl)phenylmethoxy]-1-piperidineoctanoic acid hydrochloride

Colorless crystals, mp 175°~178° C. (EtOH-AcOEt).
Analysis for $C_{27}H_{37}NO_3 \cdot HCl$: Calculated C, 70.49; H, 8.33; N, 3.04 Found C, 70.43; H, 8.31; N, 3.01

EXAMPLE 75

(±)-2-[4-[(4-Methylphenyl)phenylmethoxy]-piperidino]ethoxyacetic acid

Pale yellow liquid.
Mass spectrum m/z: 384 (M+ +1).
IR spectrum $\nu$(liq) $cm^{-1}$: 1592 (COO—)
NMR spectrum $\delta(CDCl_3)$ ppm: 1.88-2.46 (4H, m), 2.32 (3H, s), 2.88-3.38 (6H, m), 3.64-3.95 (3H, m), 4.01 (2H, s), 5.41 (1H, s), 7.00-7.40 (9H, m).

EXAMPLE 76

(±)-4-[(4-Ethylphenyl)phenylmethoxy]-1-piperidinepropionic acid hydrochloride

Colorless crystals, mp 139.5°~142.5° C. ($Me_2CO$-$Et_2O$)

Analysis for $C_{23}H_{29}NO_3 \cdot HCl$: Calculated C, 68.39; H, 7.49; N, 3.47 Found C, 68.29; H, 7.65; N, 3.52

EXAMPLE 77

(±)-4-[(4-Ethylphenyl)phenylmethoxy]-1-piperidinecaproic acid hydrochloride

Colorless crystals, mp 132°∼137° C. ($Me_2CO$).
Analysis for $C_{26}H_{35}NO_3 \cdot HCl$: Calculated C, 70.01; H, 8.14; N, 3.14 Found C, 69.81; H, 8.15; N, 3.04

EXAMPLE 78

(±)-4-[(4-n-Propylphenyl)phenylmethoxy]-1-piperidinepropionic acid hydrochloride Colorless crystals, mp 140°∼143° C. ($Me_2CO$-$Et_2O$)
Analysis for $C_{24}H_{31}NO_3 \cdot HCl$: Calculated C, 68.97; H, 7.72; N, 3.35 Found C, 68.85; H, 7.75; N, 3.29

EXAMPLE 79

(±)-4-[(4-n-Propylphenyl)phenylmethoxy]-1-piperidinecaproic acid hydrochloride

Colorless crystals, mp 136°∼138° C. ($Me_2CO$-$Et_2O$)
Analysis for $C_{27}H_{37}NO_3 \cdot HCl$: Calculated C, 70.49; H, 8.33; N, 3.04 Found C, 70.29; H, 8.32; N, 3.00

EXAMPLE 80

(±)-4-[(4-n-Butylphenyl)phenylmethoxy]-1-piperidinepropionic acid hydrochloride

Colorless crystals, mp 127°∼130° C. ($Me_2CO$-iso-$Pr_2O$).
Analysis for $C_{25}H_{33}NO_3 \cdot HCl \cdot \frac{1}{4}H_2O$: Calculated C, 68.79; H, 7.97; N, 3.21 Found C, 68.69; H, 7.98; N, 3.24

EXAMPLE 81

(±)-4-[(4-n-Butylphenyl)phenylmethoxy]-1-piperidinecaproic acid hydrochloride

Colorless crystals, mp 131°∼133° C. ($Me_2CO$-$Et_2O$)
Analysis for $C_{28}H_{39}NO_3 \cdot HCl$: Calculated C, 70.94; H, 8.50; N, 2.95 Found C, 70.68; H, 8.37; N, 2.99

EXAMPLE 82

(±)-4-[4-tert-Butylphenyl)phenylmethoxy]-1-piperidinepropionic acid hydrochloride Pale yellow crystals, mp 103°∼105° C. ($Me_2CO$-$Et_2O$).
Analysis for $C_{25}H_{33}NO_3 \cdot HCl$: Calculated C, 69.51; H, 7.93; N, 3.24 Found C, 69.50; H, 8.03; N, 3.22

EXAMPLE 83

(±)-4-[(4-tert-Butylphenyl)phenylmethoxy]-1-piperidinecaproic acid hydrochloride Colorless needles, mp 172°∼176° C. ($Me_2CO$).
Analysis for $C_{28}H_{39}NO_3 \cdot HCl$: Calculated C, 70.94; H, 8.50; N, 2.95 Found C, 70.85; H, 8.65; N, 2.87

EXAMPLE 84

4-[Bis(4-methylphenyl)methoxy]-1-piperidinecaproic acid hydrochloride

Colorless crystals, mp 136°∼140° C. (EtOH-$Et_2O$).
Analysis for $C_{26}H_{35}NO_3 \cdot HCl$: Calculated C, 70.01; H, 8.14; N, 3.14 Found C, 69.96; H, 8.23; N, 3.17

EXAMPLE 85

(±)-4-[(4-Methoxyphenyl)phenylmethoxy]-1-piperidineacetic acid

Pale yellow crystals, mp 84°∼85° C. ($H_2O$).
Analysis for $C_{21}H_{25}NO_4 \cdot 2H_2O$: Calculated C, 64.43; H, 7.47; N, 3.58 Found C, 64.70; H, 7.16; N, 3.41

EXAMPLE 86

(±)-4-[(4-Methoxyphenyl)phenylmethoxy]-1-piperidinepropionic acid hydrochloride

Colorless crystals, mp 146°∼148° C. (EtOH-AcOEt).
Analysis for $C_{22}H_{27}NO_4 \cdot HCl$: Calculated C, 65.10; H, 6.95; N, 3.45 Found C, 64.99; H, 6.83; N, 3.45

EXAMPLE 87

(±)-4-[(4-Methoxyphenyl)phenylmethoxy]-1-piperidinebutyric acid hydrochloride

Colorless crystals, mp 135°∼137° C. (EtOH-AcOEt).
Analysis for $C_{23}H_{29}NO_4 \cdot HCl \cdot \frac{1}{4}H_2O$: Calculated C, 65.08; H, 7.24; N, 3.30 Found C, 64.96; H, 7.01; N, 3.28

EXAMPLE 88

(±)-4-[(4-Methoxyphenyl)phenylmethoxy]-1-piperidinevaleric acid hydrochloride

Colorless prisms, mp 150°∼151° C. (MeOH-$Et_2O$).
Analysis for $C_{24}H_{31}NO_4 \cdot HCl$: Calculated C, 66.42; H, 7.43; N, 3.23 Found C, 66.18; H, 7.43; N, 3.26

EXAMPLE 89

(±)-4-[(4-Methoxyphenyl)phenylmethoxy]-1-piperidinecaproic acid hydrochloride

Colorless plates, mp 148°∼150° C. (MeOH-$Et_2O$).
Analysis for $C_{25}H_{33}NO_4 \cdot HCl$: Calculated C, 67.03; H, 7.65; N, 3.13 Found C, 66.84; H, 7.78; N, 3.16

EXAMPLE 90

(±)-4-[(4-Methoxyphenyl)phenylmethoxy]-1-piperidineheptanoic acid hydrochloride

Colorless crystals, mp 138°∼140° C. ($Me_2CO$-$Et_2O$).
Analysis for $C_{26}H_{35}NO_4 \cdot HCl$: Calculated C, 67.59; H, 7.85; N, 3.03 Found C, 67.41; H, 7.76; N, 3.10

EXAMPLE 91

(±)-4-[(4-Methoxyphenyl)phenylmethoxy]-1-piperidineoctanoic acid hydrochloride

Colorless prisms, mp 163°∼166° C. (EtOH-$Et_2O$).
Analysis for $C_{27}H_{37}NO_4 \cdot HCl$: Calculated C, 68.12; H, 8.05; N, 2.94 Found C, 67.97; H, 8.16; N, 2.99

EXAMPLE 92

(±)-2-[4-[(4-Methoxyphenyl)phenylmethoxy]piperidino]ethoxyacetic acid

Pale yellow liquid.
Mass spectrum m/z: 400 ($M^+ + 1$)
IR spectrum ν(liq) $cm^{-1}$: 1592 ((COO—)
NMR spectrum δ($CDCl_3$) ppm: 1.80-2.44 (4H, m), 2.88-3.36 (6H, m), 3.64-3.96 (3H, m), 3.78 (3H, s), 4.03 (2H, s), 5.40 (1H, s), 6.84 (2H, d, J=9 Hz), 7.22 (2H, d, J=9 Hz), 7.12-7.40 (5H, m).

EXAMPLE 93

(±)-4-[(4-Ethoxyphenyl)phenylmethoxy]-1-piperidinepropionic acid

Colorless crystals, mp 75°~78° C. (AcOEt-Et$_2$O).
Analysis for C$_{23}$H$_{29}$NO$_4$.H$_2$O: Calculated C, 68.80; H, 7.78; N, 3.49 Found C, 69.05; H, 7.83; N, 3.52

EXAMPLE 94

(±)-4-[(4-Ethoxyphenyl)phenylmethoxy]-1-piperidinecaproic acid

Colorless crystals, mp 110°~111.5° C. (AcOEt)
Analysis for C$_{26}$H$_{35}$NO$_4$: Calculated C, 73.38; H, 8.29; N, 3.29 Found C, 73.11; H, 8.34; N, 3.33

EXAMPLE 95

4-(Diphenylmethoxy)-1-piperidineacetic acid hydrochloride

Colorless crystals, mp 193°~194° C. (MeOH-Et$_2$O).
Analysis for C$_{20}$H$_{23}$NO$_3$.HCl: Calculated C, 66.38; H, 6.68; N, 3.87 Found C, 66.33; H, 6.71; N, 3.84

EXAMPLE 96

(±)-4-(Diphenylmethoxy)-α-methyl-1-piperidineacetic acid hydrochloride

Colorless amorphous solid, mp 63°~65° C. (Me$_2$CO-Et$_2$O)
Mass spectrum m/z: 339 (M$^+$)
IR spectrum ν(KBr) cm$^{-1}$: 1736 (COOH).
NMR spectrum δ(DMSO-d$_6$) ppm: 1.41 (3H, d, J=7 Hz), 1.62-2.30 (4H, m), 2.82-3.96 (5H, m), 3.79 (1H, q, J=7 Hz), 5.63 (1H, s), 7.07-7.55 (10H, m).

EXAMPLE 97

4-(Diphenylmethoxy)-1-piperidinevaleric acid hydrochloride

Colorless crystals, mp 150°~151° C. (H$_2$O).
Analysis for C$_{23}$H$_{29}$NO$_3$.HCl.H$_2$O Calculated C, 65.47; H, 7.64; N, 3.32 Found C, 65.50; H, 7.67; N, 3.27

EXAMPLE 98

4-(Diphenylmethoxy)-1-piperidinecaproic acid hydrochloride

Colorless pillars, mp 164°~165° C. (EtOH-Et$_2$O).
Analysis for C$_{24}$H$_{31}$NO$_3$.HCl: Calculated C, 68.97; H, 7.72; N, 3.35 Found C, 68.89; H, 7.70; N, 3.36

EXAMPLE 99

4-(Diphenylmethoxy)-1-piperidineheptanoic acid hydrochloride

Colorless prisms, mp 144°~146° C. (MeOH-Et$_2$O).
Analysis for C$_{25}$H$_{33}$NO$_3$.HCl: Calculated C, 69.51; H, 7.93; N, 3.24 Found C, 69.27; H, 7.83; N, 3.20

EXAMPLE 100

4-(Diphenylmethoxy)-1-piperidineoctanoic acid hydrochloride

Colorless plates, mp 163°~166° C. (EtOH-Et$_2$O).
Analysis for C$_{26}$H$_{35}$NO$_3$.HCl: Calculated C, 70.01; H, 8.14; N, 3.14 Found C, 69.94; H, 8.10; N, 3.13

EXAMPLE 101

2-[4-(Diphenylmethoxy)piperidino]ethoxyacetic acid hydrochloride

Colorless needles, mp 161°~162° C. (EtOH-Et$_2$O).
Analysis for C$_{22}$H$_{27}$NO$_4$.HCl: Calculated C, 65.10; H, 6.95; N, 3.45 Found C, 65.00; H, 6.87; N, 3.38

EXAMPLE 102

(±)-4-[(4-Chlorophenyl)phenylmethoxy]-1-piperidineacetic acid hydrochloride

Pale yellow amorphous solid, mp 125°~130° C. (Me$_2$CO-Et$_2$O).
Analysis for C$_{20}$H$_{22}$ClNO$_3$.HCl: Calculated C, 60.61; H, 5.85; N, 3.53 Found C, 60.62; H, 6.09; N, 3.36

EXAMPLE 103

(±)-4-[(4-Chlorophenyl)phenylmethoxy]-1-piperidinepropionic acid hydrochloride

Colorless crystals, mp 179°~181° C. (MeOH-Et$_2$O).
Analysis for C$_{21}$H$_{24}$ClNO$_3$.HCl: Calculated C, 61.47; H, 6.14; N, 3.41 Found C, 61.46; H, 6.17; N, 3.50

EXAMPLE 104

(±)-4-[(4-Chlorophenyl)phenylmethoxy]-1-piperidinevaleric acid hydrochloride

Colorless prisms, mp 142.5°~144° C. (EtOH-Et$_2$O).
Analysis for C$_{23}$H$_{28}$ClNO$_3$.HCl: Calculated C, 63.01; H, 6.67; N, 3.20 Found C, 63.05; H, 6.57; N, 3.03

EXAMPLE 105

(±)-4-[(4-Chlorophenyl)phenylmethoxy]-1-piperidinecaproic acid hydrochloride

Pale brown crystals, mp 144.5°~146° C. (Me$_2$CO).
Analysis for C$_{24}$H$_{30}$ClNO$_3$.HCl: Calculated C, 63.72; H, 6.91; N, 3.10 Found C, 63.61; H, 6.94; N, 3.08

EXAMPLE 106

(±)-4-[(4-Chlorophenyl)phenylmethoxy]-1-piperidineheptanoic acid hydrochloride

Colorless crystals, mp 136°~139° C. (Me$_2$CO-Et$_2$O).
Analysis for C$_{25}$H$_{32}$ClNO$_3$.HCl: Calculated C, 64.37; H, 7.13; N, 3.00 Found C, 64.28; H, 7.11; N, 3.07

EXAMPLE 107

(±)-4-[(4-Chlorophenyl)phenylmethoxy]-1-piperidineoctanoic acid hydrochloride

Colorless prisms, mp 187°~190° C. (EtOH-Et$_2$O).
Analysis for C$_{26}$H$_{34}$ClNO$_3$.HCl: Calculated C, 65.00; H, 7.34; N, 2.92 Found C, 65.01; H, 7.43; N, 2.95

EXAMPLE 108

(±)-2-[4-[(4-Chlorophenyl)phenylmethoxy]-piperidino]ethoxyacetic acid

Pale yellow liquid.
Mass spectrum m/z: 403, 405 (3:1, M$^+$).
IR spectrum ν(liq) cm$^{-1}$: 1596 (COO—).
NMR spectrum δ(CDCl$_3$) ppm: 1.73-2.35 (4H, m), 2.77-3.30 (6H, m), 3.55-3.89 (3H, m), 3.95 (2H, s), 5.42 (1H, s), 7.07-7.47 (9H, m).

EXAMPLE 109

(±)-4-[(3-Chlorophenyl)phenylmethoxy]-1-piperidine-propionic acid hydrochloride

Colorless crystals, mp 116°~120° C. (H$_2$O).
Analysis for C$_{21}$H$_{24}$ClNO$_3$.HCl: Calculated C, 61.47; H, 6.14; N, 3.41 Found C, 61.70; H, 6.25; N, 3.42

EXAMPLE 110

(±)-4-[(3-Chlorophenyl)phenylmethoxy]-1-piperidinebutyric acid hydrochloride

Colorless crystals, mp 134°~135° C. (Me$_2$CO-Et$_2$O).
Analysis for C$_{22}$H$_{26}$ClNO$_3$.HCl: Calculated C, 62.27; H, 6.41; N, 3.30 Found C, 62.16; H, 6.36; N, 3.39

EXAMPLE 111

(±)-4-[(2-Chlorophenyl)phenylmethoxy]-1-piperidine-propionic acid hydrochloride

Colorless crystals, mp 164°~166° C. (H$_2$O).
Analysis for C$_{21}$H$_{24}$ClNO$_3$.HCl: Calculated C, 61.47; H, 6.14; N, 3.41 Found C, 61.39; H, 6.16; N, 3.42

EXAMPLE 112

(±)-4-[(2-Chlorophenyl)phenylmethoxy]-1-piperidinebutyric acid hydrochloride

Colorless crystals, mp 154.5°~156° C. (H$_2$O).
Analysis for C$_{22}$H$_{26}$ClNO$_3$.HCl: Calculated C, 62.27; H, 6.41; N, 3.30 Found C, 62.49; H, 6.35; N, 3.34

EXAMPLE 113

(±)-4-[(4-Fluorophenyl)phenylmethoxy]-1-piperidineacetic acid

Colorless needles, mp 147°~148° C. (EtOH-Et$_2$O).
Analysis for C$_{20}$H$_{22}$FNO$_3$.H$_2$O: Calculated C, 66.47 H, 6.69; N, 3.88 Found C, 66.52; H, 6.58; N, 3.83

EXAMPLE 114

(±)-4-[(4-Fluorophenyl)phenylmethoxy]-1-piperidine-propionic acid hydrochloride

Colorless needles, mp 170°~171° C. (MeOH-Me$_2$CO).
Analysis for C$_{21}$H$_{24}$FNO$_3$.HCl: Calculated C, 64.04; H, 6.40; N, 3.56 Found C, 63.80; H, 6.39; N, 3.59

EXAMPLE 115

(±)-4-[(4-Fluorophenyl)phenylmethoxy]-1-piperidinebutyric acid hydrochloride

Colorless needles, mp 199°~200° C. (MeOH-Me$_2$CO).
Analysis for C$_{22}$H$_{26}$FNO$_3$.HCl: Calculated C, 64.78; H, 6.67; N, 3.43 Found C, 64.69; H, 6.67; N, 3.45

EXAMPLE 116

(±)-4-[(4-Fluorophenyl)phenylmethoxy]-1-piperidine-valeric acid hydrochloride

Colorless crystals, mp 181°~184° C. (EtOH-Et$_2$O).
Analysis for C$_{23}$H$_{28}$FNO$_3$.HCl: Calculated C, 65.47; H, 6.93; N, 3.32 Found C, 65.27; H, 6.61; N, 3.22

EXAMPLE 117

(±)-4-[(4-Fluorophenyl)phenylmethoxy]-1-piperidinecaproic acid hydrochloride

Colorless pillars, mp 188°~189° C. (EtOH-Et$_2$O).
Analysis for C$_{24}$H$_{30}$FNO$_3$.HCl: Calculated C, 66.12; H, 7.17; N, 3.21 Found C, 66.02; H, 7.15; N, 3.15

EXAMPLE 118

4-[Bis(4-fluorophenyl)methoxy]-1-piperidineacetic acid

Colorless needles, mp 126.5°~127.5° C. (H$_2$O)
Analysis for C$_{20}$H$_{21}$F$_2$NO$_3$.½H$_2$O: Calculated C, 64.85; H, 5.99; N, 3.78 Found C, 64.65; H, 6.27; N, 3.83

EXAMPLE 119

4-[Bis(4-fluorophenyl)methoxy]-1-piperidinepropionic acid hydrochloride

Colorless crystals, mp 166°~168° C. (H$_2$O)
Analysis for C$_{21}$H$_{23}$F$_2$NO$_3$.HCl: Calculated C, 61.24; H, 5.87; N, 3.40 Found C, 61.12; H, 5.89; N, 3.44

EXAMPLE 120

4-[Bis(4-fluorophenyl)methoxy]-1-piperidinevaleric acid hydrochloride

Pale brown needles, mp 117°~118° C. (EtOH-Et$_2$O).
Analysis for C$_{23}$H$_{27}$F$_2$NO$_3$.HCl.H$_2$O: Calculated C, 60.32; H, 6.60; N, 3.06 Found C, 60.43; H, 6.83; N, 3.13

EXAMPLE 121

4-[Bis(4-fluorophenyl)methoxy]-1-piperidinecaproic acid hydrochloride

Colorless needles, mp 129°~130° C. (EtOH-Et$_2$O).
Analysis for C$_{24}$H$_{29}$F$_2$NO$_3$.HCl.3/2H$_2$O: Calculated C, 59.93; H, 6.92; N, 2.91 Found C, 59.95; H, 6.67; N, 2.94

EXAMPLE 122

2-[4-[Bis(4-fluorophenyl)methoxy]piperidino]ethoxyacetic acid

Pale brown liquid.
Mass spectrum m/z: 405 (M+).
IR spectrum ν(liq) cm$^{-1}$: 1604 (COO−).
NMR spectrum δ(CDCl$_3$) ppm: 1.60–2.47 (4H, m), 2.73–3.40 (6H, m), 3.53–3.93 (3H, m), 3.98 (2H, s), 5.42 (1H, s), 7.00 (4H, t, J=9 Hz), 7.27 (4H, dd, J=9, 5.5 Hz).

EXAMPLE 123

4-(Diphenylmethylthio)-1-piperidinebutyric acid hydrochloride

Colorless needles, mp 196°~199° C. (EtOH-Et$_2$O).
Analysis for C$_{22}$H$_{27}$NO$_2$S.HCl.½H$_2$O: Calculated C, 63.67; H, 7.04; N, 3.38 Found C, 63.80; H, 6.82; N, 3.35

EXAMPLE 124

2-[4-(Diphenylmethylthio)piperidino]ethoxyacetic acid hydrochloride

Colorless pillars, mp 140°~142° C. (EtOH-Et$_2$O).
Analysis for C$_{22}$H$_{27}$NO$_3$S.HCl: Calculated C, 62.62; H, 6.69; N, 3.32 Found C, 62.54; H, 6.63; N, 3.31

EXAMPLE 125

(+)-4-[(4-Methylphenyl)phenylmethoxy]-1-piperidinecaproic acid hydrochloride

Colorless crystals, mp 164.5°~167° C. (H$_2$O-Me$_2$CO).
specific rotation [α]$_D^{20}$+9.5° (c=0.5, MeOH).
Analysis for C$_{25}$H$_{33}$NO$_3$.HCl: Calculated C, 69.51; H, 7.93; N, 3.24 Found C, 69.70; H, 8.07; N, 3.36

EXAMPLE 126

(−)-4-[(4-Methylphenyl)phenylmethoxy]-1-piperidinecaproic acid hydrochloride

Colorless crystals, mp 165.5°~168° C. (H$_2$O-Me$_2$CO).

specific rotation $[\alpha]_D^{20}$ −9.5° (c=0.5, MeOH).

Analysis for C$_{25}$H$_{33}$NO$_3$.HCl: Calculated C, 69.51; H, 7.93; N, 3.24 Found C, 69.50; H, 8.01; N, 3.28

EXAMPLE 127

Tablets of a pharmaceutical preparation according to the present invention are prepared in the usual manner using the following constituents:

| Compound of the present invention | 10 mg |
|---|---|
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |
| | 120 mg |

EXAMPLE 128

Capsules of a pharmaceutical preparation according to the present invention are prepared in the usual manner using the following constituents:

| Compound of the present invention | 10 mg |
|---|---|
| Lactose | q.s. |
| Calcium carboxymethylcellulose | 15 mg |
| Hydroxypropylcellulose | 2 mg |
| Magnesium stearate | 2 mg |
| | 100 mg |

EXAMPLE 129

Powder of a pharmaceutical preparation according to the present invention are prepared in the usual manner using the following constituents:

| Compound of the present invention | 20 mg |
|---|---|
| Lactose | q.s. |
| D-Mannitol | 500 mg |
| Hydroxypropylcellulose | 5 mg |
| Talc | 2 mg |
| | 1000 mg |

EXAMPLE 130

Injections of a pharmaceutical preparation according to the present invention are prepared in the usual manner using the following constituents:

| Compound of the present invention | 1 mg |
|---|---|
| Glucose | 50 mg |
| Hydrochloric acid | q.s. |
| Distilled water for injection | q.s. |
| | 2 ml |

EXAMPLE 131

Suppositories of a pharmaceutical preparation of the present invention are prepared in the usual manner using the following constituents:

| Compound of the present invention | 5 mg |
|---|---|
| Hard fat | 1295 mg |
| | 1300 mg |

EXAMPLE 132

Plasters of a pharmaceutical preparation according to the present invention

| Compound of the present invention | 10 mg |
|---|---|
| Gelatin | 1100 mg |
| Polyvinylalcohol | 250 mg |
| Methylcellulose | 100 mg |
| Glycerin | 1500 mg |
| Kaolin | 850 mg |
| Sodium polyacrylate | 50 mg |
| Polybutene | 150 mg |
| Purified water | 990 mg |
| | 5000 mg |

What is claimed is:

1. A piperidine compound represented by the following formula:

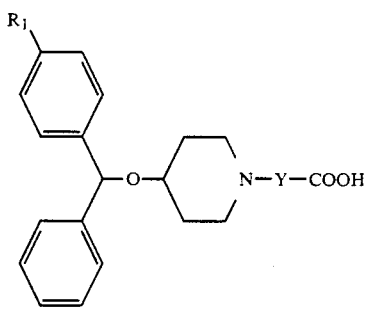

wherein R$_1$ represents a lower alkyl group and Y represents an alkylene group having 3 carbon atoms.

2. An antisematic and antiallergic agent comprising an effective amount of a piperidine derivative represented by the following formula:

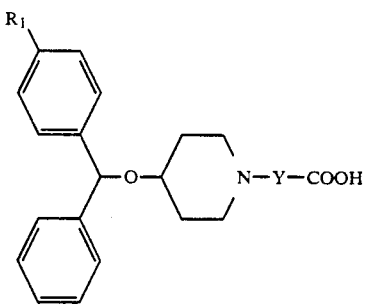

wherein R$_1$ represents a lower alkyl group and Y represents an alkylene group having 3 carbon atoms.

3. A method for the treatment of an allergic disease comprising the step of administering to a mammal an effective amount of a substance selected from the group consisting essentially of (a) a piperidine derivative represented by the following formula:

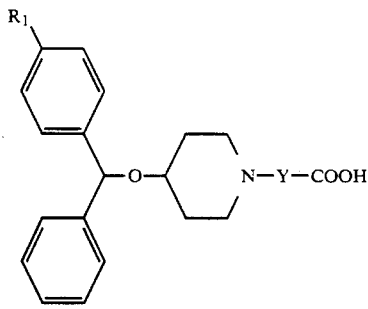

wherein $R_1$ represents a lower alkyl group and Y represents an alkylene group having 3 carbon atoms.

4. A method according to claim 3, wherein said step of administration is performed on a human being.

5. A pharmaceutical composition for the treatment of an allergic disease comprising an effective amount of a piperidine derivative represented by the following formula:

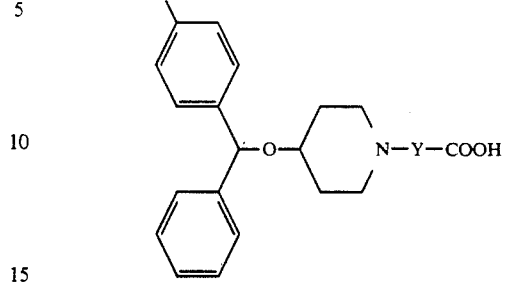

wherein $R_1$ represents a lower alkyl group and Y represents an alkylene group having 3 carbon atoms; and pharmacologically acceptable salts thereof.

* * * * *

UNITED STATES PATENT AND TRADEMARK OFFICE
CERTIFICATE OF CORRECTION

PATENT NO. : 5,153,207

DATED : OCTOBER 6, 1992

INVENTOR(S) : YASUO ITO ET AL

It is certified that error appears in the above-identified patent and that said Letters Patent is hereby corrected as shown below:

Column 5, line 26, "($\pm$)" should read --(+)--;
        line 28, "($\pm$)" should read --(+)--.

Column 6, line 62, "our" should read --out--.

Column 17, line 50, after "chloride" insert --to--.

Column 19, line 16, "$C_{27}H_{37}NO_3 \cdot C_4H_4O_4O$: should read --$C_{27}H_{37}NO_3 \cdot C_4H_4O_4$;--.

UNITED STATES PATENT AND TRADEMARK OFFICE
CERTIFICATE OF CORRECTION

PATENT NO. : 5,153,207

DATED : OCTOBER 6, 1992

INVENTOR(S) : YASUO ITO ET AL

It is certified that error appears in the above-identified patent and that said Letters Patent is hereby corrected as shown below:

Column 36, Claim 2, line 44, "antisematic" should read --antihistamine-- and "agent" should read --composition--;
line 62, after "atoms", insert --and a pharmaceutically acceptable carrier--.

Claim 3, lines 65 and 66, "substance selected from the group consisting essentially of (a) a peperidine derivative" should read --piperidine compound--.

Signed and Sealed this

Sixth Day of September, 1994

Attest:

BRUCE LEHMAN

Attesting Officer     Commissioner of Patents and Trademarks